(12) United States Patent
Mureşan et al.

(10) Patent No.: US 11,157,082 B2
(45) Date of Patent: Oct. 26, 2021

(54) METHOD, HUMAN MACHINE INTERFACE, MACHINE COMPUTING UNIT AND COMPUTER PROGRAMS TO CONTROL AT LEAST ONE ACTUATOR TO CARRY OUT AT LEAST ONE TASK

(71) Applicant: ASOCIATIA TRANSYLVANIAN INSTITUTE OF NEUROSCIENCE, Cluj Napoca (RO)

(72) Inventors: Raul-Cristian Mureşan, Cluj Napoca (RO); Vasile-Vlad Moca, Cluj Napoca (RO); Bârzan Harald, Fagaras (RO)

(73) Assignee: Asociada Transylvanian Institute of Neuroscience, Cluj Napoca (RO)

( * ) Notice: Subject to any disclaimer, the term of this patent is extended or adjusted under 35 U.S.C. 154(b) by 0 days.

(21) Appl. No.: 17/315,888

(22) Filed: May 10, 2021

(65) Prior Publication Data

US 2021/0271324 A1     Sep. 2, 2021

Related U.S. Application Data

(63) Continuation of application No. PCT/IB2019/059820, filed on Nov. 15, 2019.

(51) Int. Cl.
    *G05B 13/02*     (2006.01)
    *G06F 3/01*      (2006.01)

(52) U.S. Cl.
    CPC .......... *G06F 3/015* (2013.01); *G05B 13/0265* (2013.01)

(58) Field of Classification Search
    CPC .......................... G06F 3/015; G05B 13/0265
    See application file for complete search history.

(56) References Cited

U.S. PATENT DOCUMENTS 5,813,993 A  *  9/1998  Kaplan ................. A61B 5/16
                                                   600/544
6,660,388 B2    12/2003  Liu et al.
(Continued)

FOREIGN PATENT DOCUMENTS

CN          1203191          12/1998
CN          1446371          10/2003
(Continued)

OTHER PUBLICATIONS

Baranauskas, "What limits the performance of current invasive brain machine interfaces?," Front. Syst. Neuroscience, Apr. 29, 2014, 8:68, 10 pages.
(Continued)

*Primary Examiner* — Gary Collins
(74) *Attorney, Agent, or Firm* — Fish & Richardson P.C.

(57) ABSTRACT

This invention relates to a method to control at least one actuator to carry out at least one task comprising repetitive sequences of operations, shorter than 1000 milliseconds by acquiring of endogenously generated electrical potentials within gamma frequency range generated by the brain and/or by the muscles of the body, head, or eyes of a human user, by acquiring electrical signals with sampling rate of at least 250 samples/s, by extracting the features of the signals related to high-frequency gamma waves between 30-200 Hz, by classifying, mapping and converting the signals into actions in real time, and by sending feedback and neurofeedback to a human user to enable him to control the interface.

16 Claims, 1 Drawing Sheet

(56) References Cited

U.S. PATENT DOCUMENTS

| | | | | |
|---|---|---|---|---|
| 7,865,235 | B2* | 1/2011 | Le | A61B 5/165 |
| | | | | 600/544 |
| 8,190,249 | B1* | 5/2012 | Gharieb | A61B 5/318 |
| | | | | 600/544 |
| 10,070,799 | B2* | 9/2018 | Ang | G06F 3/015 |
| 2011/0307079 | A1* | 12/2011 | Oweiss | A61B 5/4094 |
| | | | | 623/27 |
| 2012/0296569 | A1* | 11/2012 | Shahaf | A61B 5/4064 |
| | | | | 702/19 |
| 2014/0051044 | A1* | 2/2014 | Badower | A61B 5/291 |
| | | | | 434/236 |
| 2014/0058528 | A1* | 2/2014 | Contreras-Vidal | A61B 5/291 |
| | | | | 623/25 |
| 2014/0316230 | A1* | 10/2014 | Denison | A61B 5/165 |
| | | | | 600/383 |
| 2014/0349052 | A1 | 11/2014 | Kim et al. | |
| 2015/0037567 | A1 | 2/2015 | Clear et al. | |
| 2015/0132552 | A1 | 5/2015 | Kang et al. | |
| 2018/0008145 | A1* | 1/2018 | Freer | A61B 5/245 |
| 2018/0194128 | A1 | 7/2018 | Akhter et al. | |
| 2018/0257361 | A1 | 9/2018 | Bissinger et al. | |
| 2019/0059803 | A1* | 2/2019 | Myers | A61B 5/746 |
| 2020/0023189 | A1* | 1/2020 | Gribetz | A61N 1/36196 |
| 2020/0069208 | A1* | 3/2020 | Keane | A61B 5/742 |
| 2020/0069209 | A1* | 3/2020 | Keane | A61B 5/742 |
| 2020/0073475 | A1* | 3/2020 | Keane | G06N 3/08 |
| 2020/0364539 | A1* | 11/2020 | Anisimov | G06F 3/012 |

FOREIGN PATENT DOCUMENTS

| | | |
|---|---|---|
| CN | 102675780 | 9/2012 |
| CN | 104558658 | 4/2015 |
| JP | 2010235676 | 10/2010 |
| WO | WO 2009/005975 | 1/2009 |

OTHER PUBLICATIONS

Birbaumer et al., "The Thought Translation Device (TTD) for Completely Paralyzed Patients," IEEE Transactions on Rehabilitation Engineering, Jun. 200, 8(2):190-193.

Birbaumer et al., "The Thought-Translation Device (TTD): Neurobehavioral Mechanisms and Clinical Outcome," IEEE Transactions on Neural Systems and Rehabilitation Engineering, Jun. 2003, 11(2):120-123.

Carmena et al., "Learning to Control a Brain-Machine Interface for Reaching and Grasping by Primates," PLoS Biology, Oct. 13, 2003, 1(2): 193-208.

Chapin et al., "Real-time control of a robot arm using simultaneously recorded neurons in the motor cortex," Nat. Neuroscience, Jul. 1999, 2(7):664-670.

CN Office Action in Chinese Appln. No. 201811264920.9, dated Mar. 23, 2021, 24 pages (with English translation).

Electric Fields of the Brain, 2nd ed., Nunez et al. (eds.), 2006, 626 pages.

Engelhard et al., "Inducing Gamma Oscillations and Precise Spike Synchrony by Operant Conditioning via Brain-Machine Interface," Neuron, Jan. 23, 2013, 77(2):361-375.

Fetz et al., "Operant Conditioning of Specific Patterns of Neural and Muscular Activity," Science, Oct. 22, 1971, 174(4007):431-435.

Fetz et al., "Operantly Conditioned Patterns of Precentral Unit Activity and Correlated Responses in Adjacent Cells and Contralateral Muscles," J. Neurophysiology, Mar. 1973, 36(2):179-204.

Fetz, "Are movement parameters recognizably coded in the activity of single neurons?," Behav. Brain. Sciences, 1992, 15(4):679-690.

Fetz, "Operant Conditioning of Cortical Unit Activity," Science, Feb. 28, 1969, 163(3870):955-958.

Fetz, "Volitional Control of Cortical Oscillations and Synchrony," Neuron, Jan. 23, 2013, 77(2):216-218.

Fetz, "Volitional control of neural activity: implications for brain-computer interfaces," J. Physiology, Jan. 18, 2007, 579(Pt 3):571-579.

Ghani et al., "Detection of wrist movement using EEG signal for brain machine interface," Proceedings of the 2013 International Conference on Technology, Informatics, Management, Engineering and Environment, Bandung, Indonesia, Jun. 23-26, 2013, 5-8.

Grosse-Wentrup et al., "High gamma-power predicts performance in sensorimotor-rhythm brain-computer interfaces," J. Neural Engineering, Aug. 2012, 9(4):046001, 8 pages.

Gwin et al., "Beta- and gamma-range human lower limb corticomuscular coherence," Front. Human Neuroscience, Sep. 11, 2012, 6:258, 6 pages.

Lebedev et al., "Brain-machine interfaces: Past, present and future," Trends Neurosciences, Jul. 21, 2006, 29(9):536-546.

Lobel et al., "Brain Machine Interface and Limb Reanimation Technologies: Restoring Function After Spinal Cord Injury Through Development of a Bypass System," Mayo Clin. Proceedings, May 2014, 89(5)708-714.

McFarland et al., "Spatial filter selection for EEG-based communication," Electroencephalogr. Clin. Neurophysiology, Sep. 1997, 103(3):386-394.

Moca et al., "Membrane Resonance Enables Stable and Robust Gamma Oscillations," Cereb. Cortex, Jan. 2014, 24(1):119-142.

Moca et al., "Superlets: time-frequency super-resolution using wavelet sets," bioRxiv, Mar. 21, 2019, 37 pages.

Muthukumaraswamy, "High-frequency brain activity and muscle artifacts in MEG/EEG: a review and recommendations," Front. Hum. Neuroscience, Apr. 15, 2013, 7:138, 11 pages.

Nedelcu et al., "Artifact Detection in EEG using Machine Learning," Proceedings of the 13th IEEE International Conference on Intelligent Computer Communication and Processing (ICCP), Cluj-Napoca, Romania, Sep. 7-9, 2017, 7 pages.

Nicolelis, "Actions from thoughts," Nature, Jan. 18, 2001, 409(6818):403-407.

Omlor et al., "Gamma-range corticomuscular coherence during dynamic force output," NeuroImage, Dec. 19, 2006, 34(3): 1191-1198.

Patil et al., "The Development of Brain-Machine Interface Neuroprosthetic Devices," Neurotherapeutics, Jan. 2008, 5(1):137-146.

PCT International Preliminary Report on Patentability in International Appln. No. PCT/IB2019/059081, dated Apr. 27, 2021, 7 pages.

PCT International Search Report and Written Opinion in International Appln. No. PCT/IB2019/059081, dated Feb. 6, 2020, 9 pages.

PCT International Search Report and Written Opinion in International Appln. No. PCT/IB2019/059820, dated Feb. 28, 2020, 9 pages.

Pfurtscheller et al., "Mu rhythm (de)synchronization and EEG single-trial classification of different motor imagery tasks," NeuroImage, Jan. 27, 2006, 31 (1): 153-159.

Rhythms of the Brain. 1st ed., Buzsáki (ed.), Oct. 26, 2006, 465 pages.

Schoffelen et al., "Neuronal Coherence as a Mechanism of Effective Corticospinal Interaction," Science, Apr. 1, 2005, 308(5718): 111-113.

ScientificAmerican.com [online], "6 Electronic Devices You Can Control with Your Thoughts," Dec. 1, 2012, retrieved on Nov. 17, 2019, retrieved from URL<https://www.scientificamerican.com/article/pogue-6-electronic-devices-you-can-eontrol-with-your-thoughts/>, 5 pages.

Seeber et al., "High and low gamma EEG oscillations in central sensorimotor areas are conversely modulated during the human gait cycle," NeuroImage, Mar. 24, 2015, 112:318-326.

Singer, "Neuronal Synchrony: A Versatile Code for the Definition of Relations?," Neuron, Sep. 1, 1999, 24(1):49-65.

Taylor et al., "Direct Cortical Control of 3D Neuroprosthetic Devices," Science, Jun. 7, 2002, 296(5574):1829-1832.

Wolpaw et al., "Control of a two-dimensional movement signal by a noninvasive brain-computer interface in humans," Proc. Natl. Acad. Sci. USA, Dec. 21, 2004, 101(51):17849-17854.

* cited by examiner

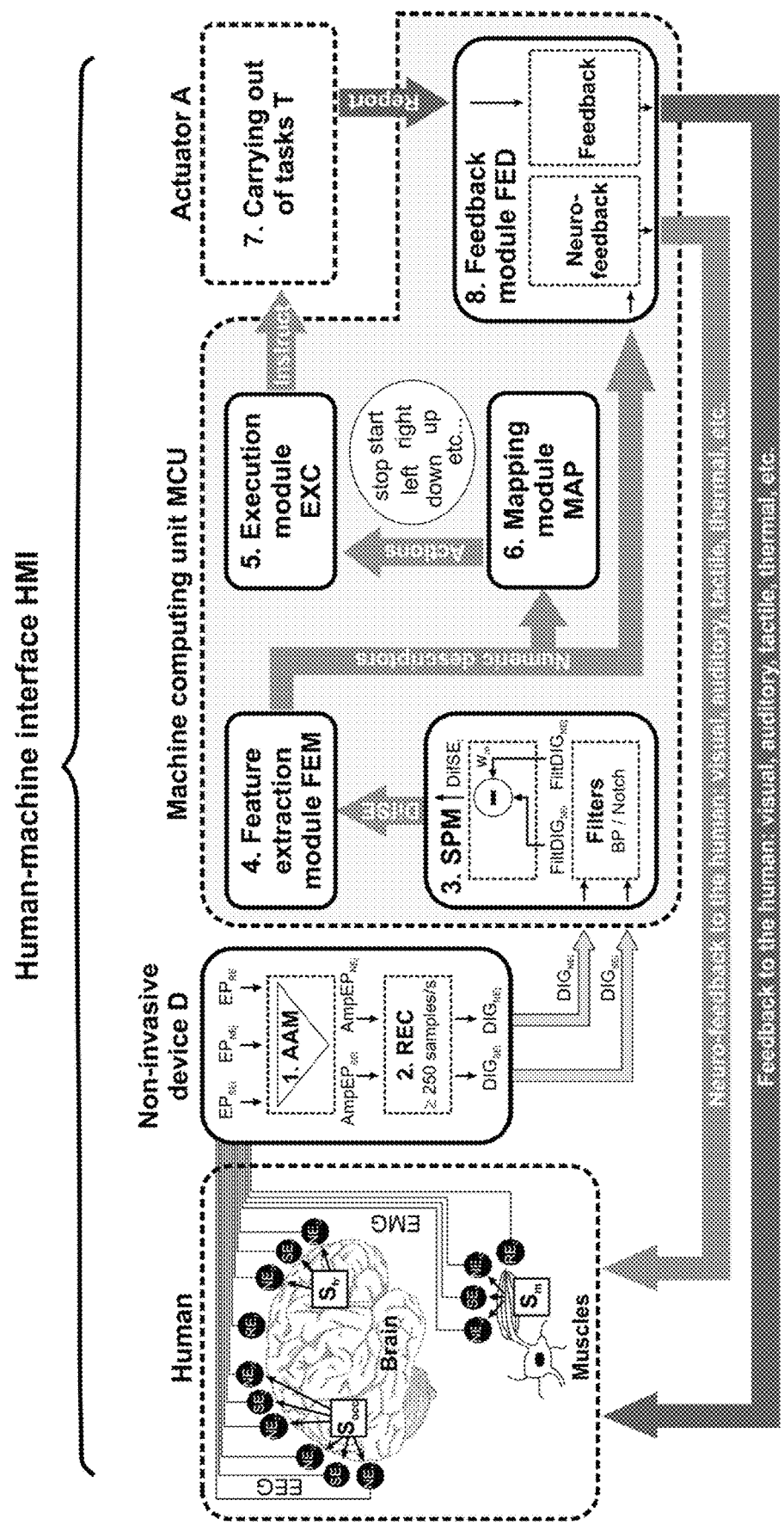

METHOD, HUMAN MACHINE INTERFACE, MACHINE COMPUTING UNIT AND COMPUTER PROGRAMS TO CONTROL AT LEAST ONE ACTUATOR TO CARRY OUT AT LEAST ONE TASK

CROSS REFERENCE TO RELATED APPLICATIONS

This application is a by-pass continuation of International Application PCT/IB2019/059820, filed on Nov. 15, 2019, which is incorporated by reference and claims the benefit of a priority application filed on Nov. 18, 2018, as Application No. PCT/IB2019/059081.

TECHNICAL FIELD

The invention is related to human-machine interfaces HMI. In particular, the invention is related to a method to control at least one actuator, to a human-machine interface for controlling at least one actuator to carry out at least one task by applying the method, to a machine computing unit and to computer programs comprising instructions that allow to carry out the operations of the method when the programs are executed.

BACKGROUND OF THE INVENTION

The projects leading to this application have received funding from the European Union's Horizon 2020 research and innovation program under grant agreement No 952096 and from the Romanian Government through the Executive Agency for Higher Education, Research, Development and Innovation Funding (UEFISCDI) under grant agreements PN-III-P4-ID-PCE-2016-0010, PN-III-P2-2.1-PED-2016-0007, and PN-III-P2-2.1-PED-2019-0277. Human-machine interfaces HMI enable humans to connect to external machines in order to carry out various tasks, without using their limbs. A brain-machine interface BMI is a special type of human-machine interface that relies on brain signals alone to control the machine. When the brain-machine interface BMI is augmented with extracranial signals, coming from outside the brain, the augmented brain-machine interface BMI becomes a human-machine interface HMI.

There are three main classes of potential applications using human-machine interfaces HMI:
First, human-machine interfaces HMI may be used for operation of the next generation computing platforms, especially for the segment of entertainment and gaming.
Second, human-machine interfaces HMI are extremely promising for assistive healthcare, offering for example solutions to bypass a defective motor pathway in patients that have suffered stroke or injury of the spinal cord.
Third, next-generation human-machine interfaces HMI may have countless industrial and scientific applications like, e.g., assisted driving, enhanced steering of aircraft, and brain-control of space suits or tools by astronauts during extra-vehicular activity EVA.

Until two decades ago, the field of brain-machine interfaces BMI has mainly focused on animal research. The lack of appropriate technology did not enable the effective implementation of working brain-machine interfaces BMI for humans.

Starting with the past decade, the field of brain-machine interfaces BMI has experienced progress both in scientific knowledge and in hardware that could support functional implementations of the brain-machine interfaces BMI.

Brain-machine interface BMI designs differ in terms of the signal features they use. Some brain-machine interfaces BMI have monitored slow waves, while others focused on faster alpha, namely with a frequency range between 8-12 Hz and beta rhythms, namely with a frequency range between 12-30 Hz.

The most common brain-machine interface BMI applications today rely on modulation of above-mentioned slow/intermediate waves, up to the beta band. Examples are applications with headsets whose sampling rate is usually below 128-256 samples/second, allowing at most beta frequencies to be realistically estimated. Ghani et al. (2013) used an EEG recording system with 256 samples/second to detect flexion and extension of the wrist based on alpha and beta waves in the range 10-30 Hz. Although the method described in Ghani et al. contains all the basic building blocks of a BMI, the usage of relatively low frequency alpha-beta waves requires quite long buffers (3 seconds in that study) to harvest enough information for control, thus limiting the real-time usage of the BMI.

On the other hand, much faster neuronal rhythms are known in neuroscience, called gamma rhythm spanning a frequency range of 30 to 200 Hz. Gamma rhythms are the oscillations most prominently associated with cognition and naturally related to movement. Cortico-muscular coherence occurs in beta and gamma bands in a motor task-specific manner and coherence in these high frequency bands is an effective cortico-spinal interaction mechanism.

Furthermore, gamma oscillations can be precisely volitionally controlled, a finding of high relevance for brain-machine interface BMI research. High gamma spectral power predicts performance in a brain-machine interface BMI setup on a trial-by-trial basis and different gamma frequencies are associated to human gait cycle in EEG. The usefulness of gamma frequencies for brain-machine interfaces BMI is demonstrated by intra-cranial signals, recorded invasively from the brain of animals, like monkeys or rats.

Gamma rhythms have a higher frequency than the slow, alpha, or beta rhythms and a fine spatial structure. In EEG, this fine spatial structure is reflected by lower information redundancy across electrodes that sample electrical potentials on the scalp. Therefore, uncorrelated and non-redundant information can be extracted in the gamma frequency range from signals recorded over different locations on the scalp. This favours a much larger putative source of information for the brain-machine interface BMI.

Another important aspect related to brain-machine interfaces BMI is the way they sample useful signals from brain sources. Invasive brain-machine interfaces BMI imply opening the skull with a craniotomy and inserting recording probes either above the cortex, using electro-corticogramE-CoG, or implanted in the cortex itself with invasive recording probes. With such invasive interfaces, monkeys can learn to move a robotic arm by controlling the activity of individual neurons or that of populations of neurons.

Invasive brain-machine interfaces BMI are rarely an option in humans, due to medical and ethical concerns. Much more often, brain-machine interface BMI applications sample brain activity from the outside of the skull, non-invasively, using electroencephalogram EEG or magnetoencephalogram MEG. As it turns out, the hardest challenge is to create non-invasive brain-machine interfaces BMI that have sufficient information transfer-rate (bandwidth) to enable real-time control of actuators.

Finally, most applications using brain-machine interfaces BMI ignore the fact that using the same signal recording technology e.g., EEG, one can pick-up extracranial signals from the level of muscles thus recording electromyogramEMG, which can be combined with the brain signals to obtain a much more capable human-machine interface HMI. These extracranial signals are usually treated as noise or artefacts and are discarded.

Terms Used in this Invention

The term "human-machine interface HMI" is used in relation to a system that is interconnected with a human user using electrical potentials endogenously generated by the human user and recorded as signals originating from the brain, called intracranial sources, and/or from muscles, called extracranial sources, and further interconnected with an external machine, called actuator.

The term "real-time", alternatively called "sub-second reaction time" is used when the duration of completion of a specific action or operation is of maximum 1 second, alternatively called 1000 milliseconds.

Disadvantages of Prior Art

The first disadvantage is that existing non-invasive brain-machine interfaces BMI can only be used to carry out very simple tasks, the tasks carried out with reaction times (delay) of over one second, being only amenable for applications such as toys and games. The reason is the severely limited information transfer rate (bandwidth) of current non-invasive brain-machine interface BMI solutions, reaching a maximum top performance of 0.25-0.5 bits/second, totally insufficient for complex applications, such as the control of actuators with multiple degrees of freedom with sub-second reaction times. The severely limited information transfer rate (bandwidth) is due to the use of the slower rhythms such as slow waves, alpha, and beta. Because they have higher spectral power, the slower rhythms recruit larger populations of neurons and propagate to larger distances, yielding a smaller number of sources of signal and providing limited information transfer rate (bandwidth) (0.25-0.5 bits/sec), which reduces their capability to be used for controlling the operation of a wide range of actuators. The second disadvantage comes from ethical and health-related issues. Brain-machine interfaces BMI can have higher information transfer rate when signals are recorded invasively, by implants introduced into the brain or when electrode sheets are implanted below the bone. Usually, invasive interfaces are ethically approved in humans only for therapeutic purposes and pose significant health risks due to potential for infection and the endogenous reaction of the brain to foreign objects. It is very unlikely that a technology involving brain surgery in healthy humans only for the purpose of controlling the operation of actuators will be legal and will gain general public acceptance.

The only feasible options for humans remain the non-invasive solutions, most frequently based on EEG. The challenge here is to extract information non-invasively from high frequency waves recorded outside of the skull, such as gamma rhythms. This is very difficult due to the attenuation of high-frequencies by the bone and scalp. In addition, in EEG spatial resolution is blurred by volume conduction.

The third disadvantage of existing brain-machine interfaces BMI is that they ignore extra-cranial signal sources, such as those originating from muscle contractions (EMG). These potentially very useful signal sources could be combined with signals that originate from the brain to obtain human-machine interfaces HMI with much larger information transfer rates.

Problem Solved by the Invention

The problem solved by the invention is to provide a method to control in real-time a wide range of actuators by using a fast human-machine interface HMI that acquires signals from a human user using non-invasive techniques, the method including the possibility to enhance the control by real-time feedback provided to the human user.

SUMMARY OF THE INVENTION

In order to solve the problem, the inventors conceived in the first aspect of the invention a method to control at least one actuator to carry out at least one task by using a human-machine interface, the method comprising repetitive sequences of 8 operations, the entire duration of each sequence being shorter than 1000 milliseconds.

Operation 1

S1.1. Acquiring continuously in time, by an acquisition and amplification module, which is part of at least one non-invasive device, of endogenously generated electrical potentials within gamma frequency range originating from at least one source of gamma waves generated by the brain and/or by the muscles of the body, head, or eyes of a human user, the electrical potentials comprising: (i) at least one source electrical potential, acquired by at least one source electrode for the at least one source corresponding to carrying out the at least one task; (ii) a selected number of neighboring electrical potentials acquired by the same selected number of neighboring electrodes for each of the at least one source electrode; (iii) at least one reference electrical potential acquired by at least one reference electrode corresponding to the at least one source electrode and its neighboring electrodes.

S1.2. Amplifying continuously in time, by the acquisition and amplification module, of the difference between electrical potentials recorded by each source electrode and its selected number of neighboring electrodes, on one hand, and a reference function, on the other hand, the reference function dependent on reference potentials recorded by their corresponding at least one reference electrode, and the amplification performed by a differential amplifier for each source electrode and its neighboring electrodes, as follows:

$$AmpEP_{SE_i} = DAmp(EP_{SE_i} - REF_m), i=\overline{1,NSE}, NSE \geq 1$$

$$AmpEP_{NE_{ij}} = DAmp(EP_{NE_{ij}} - REF_m), j=\overline{1,NNE_i}, NNE_i \geq 1$$

$$REF_m = RefFunc(EP_{RE_m}), m=\overline{1,NRE_m}, NRE_m \geq 1$$

resulting the referenced and amplified source electrical potentials corresponding to each source electrode and the referenced and amplified neighboring electrical potentials which correspond to the selected number of neighboring electrodes of each respective source electrode, S1.3. Sending continuously in time the amplified and referenced electrical source and neighboring potentials and as amplified electrical signals to a signal recording module part of the at least one non-invasive device, Operation 2

S2.1. Acquiring, by the signal recording module, which is part of the at least one non-invasive device, of the amplified electrical signals;

S2.2. Low-pass filtering the amplified electrical signals for the purpose of antialiasing;

S2.3. Digitizing the amplified and filtered signals with a sampling rate of at least 250 samples/s, and buffering the amplified, filtered, and digitized signals, Resulting digitized signals corresponding to each source electrode and digitized signals corresponding to its selected number of neighboring electrodes;

S2.4. Sending to a signal pre-processing module of a machine computing unit the digitized source signals corresponding to each source electrode, and the digitized neighboring signals corresponding to its selected number of neighboring electrodes, Operation 3

S3.1. Acquiring, by the signal pre-processing module, of the digitized source signals and their respective neighboring signals;

S3.2. Digitally filtering the digitized source signals and their respective neighboring signals by either a band-pass filter, or a notch filter, or both in order to isolate the signals in the gamma frequency range and to eliminate artefacts introduced by the power line e.g., 50 or 60 Hz, resulting filtered digitized source signals and their respective filtered digitized neighboring signals;

S3.3. Computing the difference between the filtered digitized source signals and the weighted average across their filtered digitized neighboring signals, resulting a differential signal for each source electrode of the at least one source;

S3.4. Sending each respective differential signal to a feature extraction module;

Operation 4

S4.1. Receiving, by the feature extraction module, of each respective differential signal S4.2. Placing at least every 250 milliseconds of each of the differential signal into a corresponding digital buffer, the corresponding digital buffer being updated at least every 250 milliseconds;

S4.3. Extracting at least every 250 milliseconds of at least one spectral feature of each differential signal, the at least one spectral feature referring to spectral magnitude, spectral power, spectral phase, for the purpose of quantifying the spectral properties of each respective differential signal in the gamma frequency range by:

S4.3.1. transforming each respective differential signal from the time-domain into the frequency-domain representation using spectral techniques such as the Fourier Transform, Wavelet Transform, or other, and S4.3.2. computing the at least one spectral feature referring to spectral magnitude, spectral power, spectral phase of the each respective differential signal from its frequency-domain representation within the gamma frequency range;

S4.4. Calculating at least one numerical descriptor by using the at least one spectral feature extracted in operation S4.3 and referring to spectral magnitude, spectral power, spectral phase, or any combination of the spectral features;

S4.5. Sending at least every 250 milliseconds the at least one numerical descriptor to a mapping module of the machine computing unit and, at the same time, sending the at least one numerical descriptor to a feedback module, Operation 5

S5.1. Receiving, by the mapping module, at least every 250 milliseconds of the at least one numerical descriptor;

S5.2. Associating the at least one numerical descriptor to at least one task to be carried out by at least one actuator by defining of at least one instruction;

S5.3. Sending for the at least one instruction of a corresponding action signal to an execution module of the machine computing unit, Operation 6

S6.1. Receiving, by the execution module, of the at least one action signal;

S6.2. Converting the at least one action signal into a digital or analogue instruction signal to be sent to the at least one actuator;

S6.3. Sending the at least one instruction signal to the at least one actuator;

Operation 7

S7.1. Receiving, by the at least one actuator, of the at least one instruction signal corresponding to the at least one instruction;

S7.2. Carrying out the at least one task according to the at least one instruction;

S7.3. Sending a report signal about the execution of the task according to the at least one instruction to the feedback module;

Operation 8

S8.1. Feedback:

S8.1.1. Receiving, by the feedback module, of the report signal from each at least one actuator A in respect to the execution of the at least one task according to the at least one instruction;

S8.1.2. Converting, by the feedback module, the received report signal into a feedback signal capable of being transmitted to the human user using any perceptual modality, such as visual, auditory, tactile, gustatory, or thermal and capable of being perceived by the human user;

S8.1.3. Sending the feedback signal to the human user to be used in next sequences of the method, wherein the ensemble operation 5, operation 6, operation 7 and operation 8.1 are carried out such that their total duration is less than 750 milliseconds.

S8.2. Neurofeedback:

S8.2.1. Receiving, by the feedback module, at least every 250 milliseconds of the at least one numerical descriptor calculated by the feature extraction module;

S8.2.2. Converting, by the feedback module, of the at least one numerical descriptor into a neurofeedback signal capable of being transmitted to the human user using any perceptual modality such as visual, auditory, tactile, gustatory, or thermal and capable of being perceived by the human user;

S8.2.3. Sending the neurofeedback signal to the human user to be used in next sequences of the method, in such way that the duration of the ensemble of the three sub-operations—reception of the signal, its conversion into neurofeedback signal, and the sending of the neurofeedback signal to the human user—is less than 750 milliseconds, and wherein the feedback and the neurofeedback sub-operations are executed independently from each other.

In another aspect of the invention, a human-machine interface HMI is provided for controlling at least one actuator to carry out at least one task by applying the method, which comprises at least one non-invasive device including an acquisition and amplification module arranged: (i) to acquire endogenously generated electrical potentials within gamma frequency range originating from at least one source of gamma waves generated by the brain and/or by the muscles of the body, head, or eyes of a human user (ii) to amplify the difference between electrical potentials recorded by each source electrode and by its selected number of neighboring electrodes on one hand, and a reference function over the electrical potentials recorded by the corresponding at least one reference electrode on the other hand, resulting referenced and amplified electrical source and neighboring potentials.

and (iii) to send continuously in time the amplified and referenced electrical source and neighboring potentials and as amplified electrical signals to a signal recording module analogically connected to the acquisition and amplification module.

The following electrodes are used:
at least one source electrode for the at least one source corresponding to carrying out the at least one task;
a selected number of neighboring electrodes for each of the at least one source electrode;
at least one reference electrode corresponding to the at least one source electrode and to its neighboring electrodes.

The non-invasive device also includes the signal recording module, which is arranged: (i) to acquire the amplified electrical signals from the acquisition and amplification module, (ii) to low-pass filter the amplified electrical signals for the purpose of antialiasing, (iii) to digitize the amplified and filtered signals with at least 250 samples/s, to buffer the amplified, filtered, and digitized signals, resulting digitized source signals, and digitized neighboring signals corresponding to the selected number of neighboring electrodes, (iv) to send the digitized source signals, and digitized neighboring signals to a signal pre-processing module of a machine computing unit digitally connected to the signal recording module.

The human-machine interface also comprises a computing unit, including the signal pre-processing module, the feature extraction module, the mapping module, the execution module and the feedback module.

The signal pre-processing module is configured: (i) to acquire the digitized source signals, and digitized neighboring signals; (ii) to digitally filter the digitized source signals, and digitized neighboring signals by either a band-pass filter, or a notch filter, or both in order to isolate the signals in the gamma frequency range and to eliminate artefacts introduced by the power line, e.g., 50 or 60 Hz, such as to output filtered source and respective neighboring signals and (iii) to compute the difference between each filtered digitized source signal and the weighted average across the set of its filtered digitized neighboring signals, such as to output a differential signal for each source electrode of the at least one source, and to send each respective differential signal to a feature extraction module digitally connected to the signal pre-processing module;

The feature extraction module is configured (i) to receive the differential signal corresponding to each source electrode; (ii) to place at least every 250 milliseconds of each of the differential signal into a corresponding digital buffer, the corresponding digital buffer being configured to be updated at least every 250 milliseconds; (iii) to extract at least every 250 milliseconds at least one spectral feature of each differential signal, the at least one spectral feature referring to spectral magnitude, spectral power, spectral phase; (iv) to calculate at least one numerical descriptor for each of the at least source electrode by using at least one spectral feature referring to spectral magnitude, spectral power, spectral phase or any combination of the spectral features, and (v) to send at least every 250 milliseconds the at least one numerical descriptor to a mapping module of the machine computing unit and simultaneously to a feedback module, both digitally connected to the feature extraction module.

The mapping module is configured: (i) to receive at least every 250 milliseconds the at least one numerical descriptor calculated over the features extracted from the differential signal corresponding to each source electrode; (ii) to associate the at least one numerical descriptor to at least one task to be carried out by at least one actuator by defining at least one instruction; and (iii) to send for the at least one instruction of a corresponding action signal to an execution module of the machine computing unit digitally connected to the mapping module.

The execution module is configured: (i) to receive the at least one action signal; (ii) to convert the action signal into a digital or analogue instruction signal to be sent to the at least one actuator electronically connected to the execution module; and (iii) to send the instruction signal to the at least one actuator A in order to carry out the at least one task.

The feedback module is electronically connected to the at least one actuator and digitally connected to the feature extraction module, and comprises a feedback sub-module, and a neurofeedback sub-module.

The feedback sub-module is suitable for carrying out the feedback operation of the method, and is configured: (i) to receive for each at least one actuator of a report signal corresponding to the execution of the at least one task according to the at least one instruction; (ii) to convert the report signal into a feedback signal capable of being transmitted to the human user using any perceptual modality such as visual, auditory, tactile, gustatory, or thermal and capable of being perceived by the human user; and (iii) to send the feedback signal to the human user to be used in next sequences of the method.

The machine computing unit is configured such that the duration of the ensemble operation 5, operation 6, operation 7 and operation 8.1 is less than 750 milliseconds.

The neurofeedback sub-module is suitable for carrying out the neurofeedback operation of the method, and is configured to: (i) to receive at least every 250 milliseconds the at least one numerical descriptor computed by the feature extraction module; (ii) to convert the at least one numerical descriptor into a neurofeedback signal capable of being transmitted to the human user using any perceptual modality such as visual, auditory, tactile, gustatory, or thermal and capable of being perceived by the human user, and (iii) to send the neurofeedback signal to the human user to be used in next sequences of the method;
The neurofeedback sub-module is configured in such way that the duration of the ensemble of the three sub-operations—reception of the signal, its conversion into neurofeedback signal and the sending of the feedback signal to the human user—is less than 750 milliseconds.
The machine computing unit is configured such that the feedback operation and the neurofeedback operation are executable independently from each other.

The human-machine interface also comprises the at least one actuator electronically connected to the machine computing unit, and arranged to: (i) receive from the execution module of the instruction signal corresponding to the at least one task; (ii) to carry out the at least one task; (iii) to send to the feedback module the report signal about the execution of the at least one task according to the at least one instruction.

In another aspect of the invention, it is provided a machine computing unit configured to carry out the operations 3 to 6 and operation 8 of the method in order to process endogenously generated electrical potentials within gamma frequency range originating from at least one source of gamma waves generated by the brain and/or by the muscles of the body, head, or eyes of a human user such as to send at least one instruction for carrying at least one task by at least one actuator.

In another aspect of the invention, it is provided a computer program comprising instructions which, when the program is executed by a first computer causes the first computer to encode data by performing operation 1 and 2 of the method according to any of the claims 1 to 5 and to transmit the encoded data to a second computer.

In another aspect of the invention, it is provided a computer program comprising instructions which, when the program is executed by a second computer causes the second computer to receive encoded data from the first computer and decode the received data by performing operation 3 to 6 of the method according to any of the claims 1 to 5, to transmit the encoded data to a third computer for carrying out operation 7 of the method, to receive encoded data from the third computer regarding the execution of operation 7 and decode the received data by performing operation 8 of the method.

In another aspect of the invention, it is provided a computer program comprising instructions which, when the program is executed by a third computer causes the third computer to receive encoded data from the second computer by performing operation 7 of the method according to any of the claims 1 to 5 and to transmit the encoded data to the second computer in order to carry out operation 8 of the method.

Advantageous Effects of the Invention

By using the invention, it is possible for the human user to control the operation of a wider range of actuators and for each actuator to execute a wider range of tasks than in case the control was made only by using the limbs of the human user. Using volitionally-induced signals from sources of human neural and muscular activity to control the operation has the technical effect of increasing the number of actuators and the number of tasks than can be controlled By using the invention, it is possible for the human user to control the operation of the wider range of actuators by using volitionally-induced signals from sources of human neural activity without the need to use invasive techniques in order to obtain the signals from the human user;

By using the invention, it is possible to control the operation of the wider range of actuators much faster than with existing methods, enabling their real-time control;

By using more than one source of signals of human neural and muscular activity, originating from the brain and/or from the muscles of the body, head, or eyes of the human user, it is possible to adapt the method to a large variety of needs to control the operation of the actuators.

By using the invention, it is possible to obtain full flexibility of the control of the wider range of actuators adapted to the particulars of each human user.

BRIEF DESCRIPTION OF THE DRAWINGS

FIG. 1 depicts a combined diagram of the method and human-machine interface HMI

DETAILED DESCRIPTION OF THE INVENTION INCLUDING DESCRIPTION OF EMBODIMENTS

In order to solve the problem, the inventors sought to find a source of waves generated by the brain and/or by the muscles of the body, head, or eyes of a human user, capable to be volitionally modulated by the human user, to be associated to cognition and movement, and to be capable to carry sufficient information to control in real-time the movement of one or several actuators A to carry out one or more tasks T with sub-second reaction time. For this purpose, the inventors turned their attention to gamma waves generated by the brain and/or by the muscles of the body, head, or eyes of the human user that do satisfy the conditions of being associated with volition, cognition, and movement and of being capable to carry sufficient information.

Throughout this invention, the term "source S of gamma waves" or, alternatively, "source" S refers to a source of gamma waves generated by the human brain or the muscles of the human body, head, or eyes of the human user.

For the easy understanding of the invention, unless the contrary is explicitly mentioned, the following simplifications are made:

The "actuator A" stands for one or more actuators A. The number of actuators A is not limited by the invention, it depends only on the purpose for which the actuators A are being used;

The "task T" stands for one or more tasks T to be carried out by the actuator A. The number of tasks for each actuator A is not limited by the invention—it depends on the purpose for which the tasks T are defined;

The "source" S of gamma waves stands for one or more sources S of gamma waves;

The "non-invasive device D" stands for one or more non-invasive devices D.

The gamma waves used in the invention have a frequency range between 30 and 200 Hz. Gamma frequency range can be further divided for the purpose of better understanding of the teaching of the invention in sub-ranges, alternatively called sub-bands. There are two terms associated with these sub-ranges defined as follows:

The term "narrow-band gamma waves" refers to a sub-band spanning an extent (width) of maximum 40 Hz, for example between 30 Hz and 70 Hz or between 90 Hz and 115 Hz.

The term "broad-band gamma waves" refers to a sub-band spanning a frequency range larger than 40 Hz, i.e. broad-band gamma may span between 30 Hz and 120 Hz or between 120 Hz and 200 Hz.

There are two major potential types of sources S of gamma waves: muscular signals and cortical gamma bursts. Body, eyes, and head muscles produce broad-band gamma activity induced by oscillations and spikes. On the other hand, the inventors have shown that cortical gamma bursts are well localized spatially, being generated by local cortical circuits, their frequency being narrow-band and typically well localized in time, that is, they occur in bursts.

Thus, gamma waves have as intrinsic characteristic the fact that they can be produced as a consequence of local oscillations in the brain and/or by muscles controlling body, head, or eyes.

By contrast to other frequency ranges, like slow (<0.5 Hz), delta (0.5-4 Hz), theta (4-8 Hz), alpha (8-12 Hz), or beta (12-30 Hz), gamma spans a much wider frequency range, from 30 to 200 Hz. The consequence of all these properties of gamma is that multiple simultaneous gamma oscillations are possible, localized in various parts of the brain/scalp/body, and spanning various frequency sub-bands. This leads to the possibility of controlling a much wider range of actuators A, and for each actuator A, to carry out a wider range of tasks T than it is possible with lower frequency waves, that is <30 Hz. Yet another intrinsic characteristic of gamma waves is the fact that they can be rapidly modulated, thus facilitating smaller reaction times than in case of slower waves, like slow, delta, theta, alpha, and beta waves. Prior art did not prompt for electing gamma waves as support of the information to control the wide range of actuators A because of inherent technical limitations of the prior art in estimating and using higher frequency range waves, such as gamma, by non-invasive techniques.

Traditional non-invasive techniques, such as electroencephalogram EEG are able to record lower frequency range waves, such as slow waves, alpha, and beta, because the lower frequency range waves have higher spectral power, are not as much attenuated by the bone and scalp, and are thus capable to propagate through the skull to reach the recording electrodes. Modulations of the lower frequency range waves also last for much longer durations, typically on the order of hundreds of milliseconds to seconds.

In contrast, gamma waves originating from the brain are characterized by narrow-band spectral power that cannot be sustained for very long time, typically appearing in brief bursts.

In addition, because of their higher frequency, gamma waves are more attenuated, that is, filtered out by the skull and tissue than slower waves. Therefore, it is very difficult to detect gamma waves originating in the brain by most non-invasive recording devices, such as electroencephalogram EEG, in such a way that the electrical signals corresponding to the gamma waves carry sufficient information to be processed further for the purpose of converting them into one or more tasks T.

In other words, although the intrinsic characteristics of gamma waves favour their use for the purpose of controlling a wide range of actuators A at sub-second reaction times, the technical limitations of the state of the art in detecting, isolating and estimating brief bursts of gamma waves using non-invasive techniques did not prompt the person skilled in the art to using gamma waves for the purpose of converting them into one or more tasks T.

The inventors conceived a way to enable human users to enhance the volitional generation of endogenous gamma waves, to extract and process electrical signals corresponding to the gamma waves originating from one or more sources S, in such a way that the output signal is able to carry sufficient information to allow controlling of the wide range of actuators A to carry out a wide range of tasks T. The new technical effects are explained in detail throughout the invention as disclosed and claimed.

The method of the invention controls one or more actuators A for carrying out one or more tasks T by using a human-machine interface HMI for acquiring and transforming endogenously generated electrical potentials within gamma frequency range originating from one or more sources S of gamma waves into instructions for each of the tasks T.

Before beginning the method, the purpose for which the method is used has to be selected, in order to choose the actuators A, the tasks T, and the sources S.

The actuator A is a component of a device or a distinct machine that is responsible for controlling the movement of one or more objects, mechanisms or systems, including limbs.

The movement can be real or virtual. Furthermore, the actuator A is not limited to the control of movement but it can also be a component of a device or a distinct machine that executes any kind of actions, such as emitting sounds for example.

Once the actuator A and the task T are defined, the source or sources S are selected, then the non-invasive device D must be configured. The configuration of the non-invasive device D is presented in detail in the section referring to the second aspect of the invention.

With reference to FIG. 1, the method comprises repetitive sequences of 8 operations for converting the endogenously generated electrical potentials within gamma frequency range into instructions for the actuator A to carry out the task T. The entire duration of each sequence of operations of the method is shorter than 1000 milliseconds.

For the ease of understanding of the method, in the detailed description of the method unless the contrary is explicitly mentioned, the following simplifications are made:

"Source electrodes i $SE_i$ shall stand for one or more source electrodes;

"Neighboring electrodes j $NE_{ij}$ shall stand for one or more neighboring electrodes;

"Reference electrodes" m $RE_m$ shall stand for one or more reference electrodes;

"Signals" shall stand for one or more signals.

Operation 1 of the method is carried out by the non-invasive device D and has three sub-operations. The input and output time-domain signals of this operation are analogue.

In the first sub-operation, an acquisition and amplification module AAM of the non-invasive device D acquires continuously in time from the brain and/or by the muscles of the body, head, or eyes of the human user the endogenously generated electrical potentials:

One or more source electrical potentials $EP_{SE_i}$, by a corresponding source electrode i $SE_i$, of the source S for carrying out the task T, one electrical potential $EP_{SE_i}$ corresponding to each source electrode i $SE_i$;

A selected number of neighboring electrical potentials $EP_{NE_{ij}}$ by a corresponding selected number of neighboring electrodes j $NE_{ij}$ corresponding to each source electrode i $SE_i$;

One or more reference electrical potentials $EP_{RE_m}$ by one or more reference electrodes m $RE_m$ corresponding each source electrode i $SE_i$ and its neighboring electrodes j $NE_{ij}$, In the second sub-operation, the acquisition and amplification module AAM carries out continuously in time the amplification of the difference between the electrical potentials $EP_{SE_i}$, recorded by each source electrode i $SE_i$, and its selected number of neighboring electrical potentials $EP_{NE_{ij}}$, recorded by its neighboring electrodes $NE_{ij}$, on one hand, and a reference function RejFunc, on the other hand, the reference function dependent on reference electrical potentials $EP_{RE_m}$ recorded by the corresponding reference electrodes m $RE_m$. This is carried out by using a differential amplifier Damp for each source electrode i $SE_i$ and each of its neighboring electrodes j $NE_{ij}$, as follows:

$$AmpEP_{SE_i} = DAmp(EP_{SE_i} - REF_m), i = \overline{1, NSE}, NSE \geq 1$$

$$AmpEP_{NE_{ij}} = DAmp(EP_{NE_{ij}} - REF_m), j = \overline{1, NNE_i}, NNE_i \geq 1$$

$$REF_m = RefFunc(EP_{RE_m}), m = \overline{1, NRE_m}, NRE_m \geq 1$$

resulting the referenced and amplified source electrical potential AmpEP$_{SE_i}$ corresponding to each source electrode i SE$_i$ and the referenced and amplified neighboring electrical potentials AmpEP$_{NE_{ij}}$ which correspond to the selected number of neighboring electrodes j NE$_{ij}$ of each respective source electrode i SE$_i$.

In the third sub-operation referenced and amplified source and electrical source potentials AmpEP$_{SE_i}$ and respective referenced and amplified neighboring electrical potentials AmpEP$_{NE_{ij}}$ are being sent continuously in time as amplified electrical signals to a signal recording module REC part of the non-invasive device D.

In the first sub-operation of operation 2 of the method, the signal recording module REC acquires the amplified electrical signals corresponding to the referenced and amplified source electrical potential AmpEP$_{SE_i}$ and, respectively, the referenced and amplified neighboring electrical potentials AmpEP$_{NE_{ij}}$.

In the second sub-operation, the signal recording module REC low-pass filters the amplified electrical signals for the purpose of antialiasing.

In the third sub-operation, the signal recording module REC digitizes the amplified and filtered signals with at least 250 samples/s, and buffers the amplified, filtered, and digitized signals.

The output of operation 2 are the digitized source signals, DIG$_{SE_i}$ corresponding to each source electrode i SE$_i$ and digitized neighboring signals DIG$_{NE_{ij}}$ corresponding to the selected number of neighboring electrodes j NE$_{ij}$.

The amplified, filtered, and digitized source and respective neighboring signals DIG$_{SE_i}$ and DIG$_{NE_{ij}}$ are sent in the fourth sub-operation to a signal pre-processing module SPM of a machine computing unit MCU.

In operation 3 of the method, the signal pre-processing module SPM acquires in the first sub-operation the amplified, filtered, and digitized source and respective neighboring signals DIG$_{SE_i}$ and DIG$_{NE_{ij}}$.

Then, in the second sub-operation, the signal pre-processing module SPM digitally filters the amplified, filtered, and digitized source and respective neighboring signals DIG$_{SE_i}$ and DIG$_{NE_{ij}}$ by either a band-pass filter, or a notch filter, or both band-pass and notch filter in order to isolate the signals in the gamma frequency range and to eliminate artefacts introduced by the power line e.g., 50 or 60 Hz, resulting filtered digitized source and respective filtered digitized neighboring signals FiltDIG$_{SE_i}$ and FiltDIG$_{NE_{ij}}$.

In the third sub-operation, the signal pre-processing module SPM computes the difference between the filtered digitized source signal FiltDIG$_{SE_i}$ corresponding to each source electrode i SE$_i$ and the weighted average across the filtered digitized neighboring signals FiltDIG$_{NE_{ij}}$ corresponding to its selected neighboring electrodes j NE$_{ij}$ resulting a differential signal DifSE$_i$ for each source electrode i SE$_i$ of the source S.

Then, in the fourth sub-operation, the signal pre-processing module SPM sends each differential signal DifSE$_i$ to a feature extraction module FEM of the machine computing unit MCU digitally connected to the signal pre-processing module SPM.

In a preferred embodiment, the computation in the third sub-operation of operation 3 of the difference between the filtered digitized signal FiltDIG$_{SE_i}$ corresponding to each source electrode i SE$_i$ and the average across the filtered digitized neighboring signals FiltDIG$_{NE_{ij}}$ corresponding to its neighboring electrodes j NE$_{ij}$ is carried out using the formula:

$$DifSE_i = FiltDIG_{SE_i} - \sum_{j=1}^{NNE_i} w_j \cdot FiltDIG_{NE_{ij}}, NNE_i \geq 1$$

where,

DifSE$_i$ is the resulting differential signal for each source electrode i SE$_i$ of the at least one source S;

FiltDIG$_{SE_i}$ is the filtered digitized source signal corresponding to each source electrode i SE$_i$ of the at least one source (S);

NNE$_i$ is the selected number of neighboring electrodes j NE$_{ij}$ corresponding to each source electrode i SE$_i$;

w$_j$ are weighting factors for the neighboring electrodes j NE$_{ij}$;

FiltDIG$_{NE_{ij}}$ are the filtered digitized neighboring signals corresponding to neighboring electrodes j NE$_{ij}$ of each respective source electrode i SE$_i$.

In operation 4 of the method the feature extraction module FEM receives in the first sub-operation each differential signal DifSE$_i$ corresponding to the source electrode i SE$_i$ of the source S.

In the second sub-operation, the feature extraction module FEM places at least every 250 milliseconds each differential signal DifSE$_i$ into a corresponding digital buffer. If more than one source electrode i SE$_i$ is used, than all differential signals DifSE$_i$, each one corresponding to its source electrode i SE$_i$ are placed together at the same time into their corresponding digital buffers. The digital buffer/buffers is/are updated at least every 250 milliseconds.

Then, in the third sub-operation, the feature extraction module FEM extracts at least every 250 milliseconds one or more spectral features of each differential signal DifSE$_i$ corresponding to each one source electrode i SE$_i$ of the at least one source S. The spectral features refer to spectral magnitude, spectral power, spectral phase, for the purpose quantifying the dynamical properties of the differential signal DifSE$_i$ in the gamma frequency range. Extraction is made by:

firstly, transforming the time-domain each differential signal DifSE$_i$ into frequency-domain representation using spectral techniques such as the Fourier Transform, Wavelet Transform, or other;

secondly, computing one or more spectral features referring to spectral magnitude, spectral power, spectral phase, of each differential signal DifSE$_i$ from the frequency-domain representation within the gamma frequency range.

In the fourth sub-operation, depending on the tasks T to be accomplished by the actuator A, the feature extraction module FEM calculates one or more numerical descriptors for each of the at least one source electrode i SE$_i$ by using one or more spectral features referring to spectral magnitude, spectral power, spectral phase, or any combination of the corresponding spectral features.

The descriptors have two purposes: on one hand they serve as carrier of information for the instruction, and on the other hand they serve as instrument for the human user to be trained such that he can adjust and optimize the endogenously generated electrical potentials in the gamma frequency range for a given task T.

For this purpose, the feature extraction module FEM sends, in the fifth sub-operation at least every 250 milliseconds the one or more numerical descriptors to a mapping module MAP of the machine computing unit MCU and at the same time sends the same numerical descriptors to a feedback module FED of the machine computing unit MCU.

In another preferred embodiment, in the third sub-operation of operation 4, one or more bivariate features are further extracted, where one bivariate feature corresponds to one pair of differential signals $DifSE_{i1}$ and $DifSE_{i2}$. Each bivariate feature refers to the phase relation between the signals of each respective pair of differential signals $DifSE_{i1}$ and $DifSE_{i2}$, corresponding to at least two source electrodes i1 $SE_{i1}$ and i2 $SE_{i2}$. The purpose of extracting bivariate features is to obtain in the fourth sub-operation of operation 4 one or more numerical descriptors which quantify the phase relation between gamma waves generated at different spatial locations across the human user's head and/or body. The extracting of the bivariate features takes place in a similar way with the extraction of the spectral features and simultaneously with the extraction of spectral features:

firstly, each pair of differential signals $DifSE_{i1}$ and $DifSE_{i2}$ is transformed from the time-domain into frequency-domain representation using spectral techniques such as the Fourier Transform, Wavelet Transform, or other, and secondly, each bivariate feature is additionally computed referring to the phase relation between the signals of the at least one pair of differential signals $DifSE_{i1}$ and $DifSE_{i2}$.

In the same preferred embodiment, in the fourth sub-operation of operation 4 one or more numerical descriptors are further calculated, respectively, using the one or more bivariate features.

Importantly, the phase relation between gamma waves from different brain sources can change dynamically during cognitive processing. Therefore, the phase relation can be a robust property that the human user can modulate in order to provide a communication channel through the human machine interface HMI.

In another preferred embodiment, in the third sub-operation of operation 4, apart from one or more spectral features, of one or more multivariate features are extracted, each multivariate feature referring to the entropy, complexity, or fractal dimension across one or more differential signals $DifSE_i$ corresponding to each source electrodes i $SE_i$. The extraction of the features is carried out in two operations:

when only one differential signal $DifSE_i$ is available, the signal is embedded in a first stage with a certain time lag to obtain multiple signals, or, when more than one differential signal is available taking the plurality of differential signals $DifSE_i$ as they are, and in the second stage the entropy, complexity, or fractal dimension across the vectors constructed is computed by aggregating the samples at each time point of the multiple signals resulting from the first stage.

In the same preferred embodiment the sub operations of embedding and computing in respect to the entropy, complexity or fractal dimension are carried out simultaneously with carrying out the operations of extraction and computing of the spectral features.

In the same preferred embodiment, the fourth sub-operation of operation 4 one or more numerical descriptors are calculated by using one or more multivariate features referring to entropy, complexity, or fractal dimension across one or more differential signals $DifSE_i$ or any combination of the corresponding multivariate features.

The advantage of using multivariate features is related to the fact that the global brain state can also change dynamically and the amount and complexity of processing may be reflected in the overall properties of this dynamical state-space. The latter can be well characterized by measures of entropy, complexity, or fractal dimension, computed over multiple signals that reflect the dynamics of the sources. These features can provide complementary information to the spectral features and have the advantage of informing the machine computing unit MCU about the global brain state. As a result, the human-machine interface HMI can be designed to provide an adaptive mapping from numerical descriptors to action signals, depending on the state of the brain.

The processing of the signals as carried out in the third and fourth operation of the method allow the isolation of the signals in the gamma frequency range originating from each source electrode i $SE_i$ of each source S, without using invasive techniques, in such a way to overcome the limitations of prior art in isolating signals in gamma frequency range, because gamma waves are attenuated by the skull and tissue to much more extent than slower waves.

The real-time extraction of the spectral, bivariate and multivariate features of the differential signals $DifSE_i$ adapted for each task T and adapted to each human user allows a large flexibility in applying the invention to a wide category of tasks T. For each task T, a particular feature among the spectral, bivariate, and multivariate features may be relevant or a combination of two or more features.

The fact that the method allows defining one or a plurality of numerical descriptors has the advantage of combining the spectral, bivariate, and multivariate features of the differential signal $DifSE_i$ corresponding to each source electrode i $SE_i$, obtaining in this way a new and surprising effect of maximizing the information bandwidth extracted from the endogenously generated electrical potentials within gamma frequency range originating from one or more specific sources of gamma waves generated by the brain and/or by the muscles of the body, head, or eyes of the human user. As a consequence of the effect of maximizing the extracted information bandwidth, it is possible to adapt the method to a large variety of needs to control the operation of the actuators and it is possible to obtain full flexibility of the control of the wider range of tasks adapted to the particulars of each human user.

In the fifth sub-operation of operation 4, the feature extraction module FEM sends at least every 250 milliseconds the numerical descriptor or descriptors to a mapping module MAP of the machine computing unit MCU and, at the same time, sends the numerical descriptor or descriptors to a feedback module FED.

In the first sub-operation of operation 5, the mapping module MAP receives at least every 250 milliseconds the numerical descriptor or descriptors.

Then, in the second sub-operation, the mapping module MAP associates to each of the numerical descriptors one task T to be carried out by the actuator A by defining an instruction corresponding to the task. Thus, to each numerical descriptor corresponds a specific instruction to carry out a specific task T. The instruction as a result of the association is sent in the third sub-operation as an action signal to an execution module EXC of the machine computing unit MCU.

In a preferred embodiment, the association in S5 may be carried out either by direct mapping of numerical descriptors onto instructions or by interposing between the numerical descriptors and the instructions at least one classifier, e.g., neural network, support vector machine, decision tree, or any type of classifier, previously trained to perform a specific mapping using machine learning.

In operation 6 of the method the execution module EXC receives in the first sub-operation each action signal, converts in the second sub-operation the action signal into a corresponding instruction signal and sends in the third sub-operation the instruction signal to the actuator A. The instruction signal may be analogue or digital, the choice between the two types depending on the type of each actuator A. For example, if the actuator A is a motor, the instruction signal will be an analogue signal, whereas if the actuator A is a pointer on a screen, the instruction signal will be a digital one.

In operation 7 of the method the actuator A receives in the first sub-operation the instruction signal corresponding to each instruction and carries out in the second sub-operation the task T corresponding to each instruction received. Then, in the third sub-operation, the actuator A sends to the feedback module FED a report signal about the execution of the task T corresponding to each instruction signal received.

Operation 8 of the method is a feedback operation. Its role is to provide the human user with information about the execution of the task T corresponding to each instruction received. The feedback is used for the ensuing sequences of the method.

There are two types of feedback operations: feedback operations 8.1 and neurofeedback operations 8.2, each one of them comprising three sub-operations. The feedback operations 8.1 and the neurofeedback operations 8.2. are executed independently from each other. The feedback is associated to the actuator A that carried each task T, whereas the neurofeedback is associated to the numerical descriptor associated with the task T.

The purpose of the feedback is to inform the human user about the carrying out of each task T, whereas the purpose of the neurofeedback is to inform the human user about the properties of the gamma waves that his source S has generated in order to carry out the task T.

In case of the feedback, in the first sub-operation of operation 8, the feedback module FED receives, from the actuator A, the report signal with respect to the execution of each task T, then in the second sub-operation the feedback module FED converts the received report signal into a feedback signal capable of being transmitted to the human user using any perceptual modality such as visual, auditory, tactile, gustatory, or thermal, and capable of being perceived by the human user. The feedback signal is being sent to the human user in the third sub-operation.

In order to control the the operation of the wider range of actuators in real-time, the carrying out of the operations 5,6,7 and 8 by the feedback module is such that the duration of the ensemble of the operations 5,6,7 and 8 is less than 750 milliseconds. The threshold of 750 milliseconds is related to the timescale of human perception.

In case of the neurofeedback, the feedback module FED
receives in the first sub-operation of operation 8 at least every 250 milliseconds of the numerical descriptor or descriptors calculated by the feature extraction module FEM. The feedback module FED converts in the second sub-operation the numerical descriptor or descriptors into a neurofeedback signal capable of being transmitted to the human user using any perceptual modality such as visual, auditory, tactile, gustatory, or thermal, and capable of being perceived by the human user.

The neurofeedback signal is sent in the third sub-operation to the human user to be used in next sequences of the method.

The duration of the ensemble of the three sub-operations—reception of the signal, its conversion into neurofeedback signal and the sending of the feedback signal to the human user—is less than 750 milliseconds.

The way the feedback and/or respectively neurofeedback reach the human user depends on a plurality of factors: on the type of task, on the human user himself, and on the availability of devices that may help display the feedback and/or respectively neurofeedback. For example, if visual feedback and/or neurofeedback is contemplated, this may be carried out by rendering an image on a monitor, or moving a visual gauge, or modulating the intensity of an LED. If auditory feedback and/or respectively neurofeedback is contemplated, this may be carried out by using a loudspeaker for transmitting tones or rhythms corresponding to the execution of each task. If tactile feedback and/or respectively neurofeedback is contemplated, this may be carried out by manipulating the vibrations of an array of pressure skin stimulators. If the human user is blind, then tactile and/or auditory feedback and/or respectively neurofeedback may be selected. The method allows any combinations, such as but not limited to visual for the feedback and auditory for the neurofeedback, etc.

The method according to the invention, as described above is totally deterministic, that is, for given values of the endogenously generated electrical potentials within gamma frequency range that enter as input in the first operation of the method, the same signal will be sent at the end of the sixth operation to each actuator A for carrying out the same task T.

The method as described above refers to its operational phase. When the human user is confronted for the first time with the need to control the actuator A in order to carry out one or more tasks T by the human-machine interface HMI according to the operations of the method, he may need a training phase before the operational phase in order to train his sources S to produce the endogenously generated electrical potentials within the specific gamma frequency range such that the signals sent at the end of the sixth operation to each actuator A for carrying out the task T have the appropriate characteristics necessary for carrying out the task T The presence of the neurofeedback in operation 8 allows the human user to adjust during the training phase the minimum required levels of the endogenously generated electrical potentials within gamma frequency range necessary for carrying out the task T.

The method allows overcoming limitations of prior art through both specific operations and by the global succession of operations. As such, operation 2 enables a high-enough sampling rate to allow for the correct evaluation of gamma frequency waves in the recorded signals, that is sampling rate >250 samples/s. Then, the computation of the differential signals $DifSE_i$ in operation 3 allows isolating local gamma wave sources with increased spatial resolution and reducing redundancy over the source electrodes i $SE_i$. Next, operation 4 enables the characterization of the gamma waves generated by the subject using numerical descriptors that are computed fast enough, at least every 250 milliseconds, to allow for the volitional fast modulation of the waves by the human user and enable the observation of the human of this modulation. To this end, the numerical descriptors are sent to a neurofeedback procedure in operation 8.2 every 250 ms, which then informs the human user within less than 750 ms. As a result, the closed loop enables the human user to directly increase the gamma waves he generates such as to reach the source electrodes i $SE_i$, overcoming the attenuation of the gamma waves by the skull and skin. The neurofeedback operations 8.2. provide the fast information that enables the human user to discover strategies to generate powerful enough gamma waves that propagate through the skull. Coupled with the feedback of operation 8.1 about the execution of the action, the method enables the human user to develop precise strategies to control in real-time the actuator A to carry out the task T. Finally, the mixing of brain sources with extracranial sources from muscles offers a further boost to the information transfer rate of the system and allows a flexible combination of features to be used for complex control of a wide range of actuators A, much faster than with existing methods, enabling real-time control.

In a second aspect of the invention it is provided a system for applying the method.

The system, called human-machine interface HMI, comprises one or more non-invasive devices D, a machine computing unit MCU, and one or more actuators A. Hereafter, the same simplification as in case of the method will be applied, one non-invasive device D shall stand for one or more non-invasive devices D and one actuator A shall stand for one or more actuators A The non-invasive device D and the actuator A are devices from the prior art that are arranged for carrying out operations of the method, as it will be detailed below. The machine computing unit MCU is a new component that does not exist in the absence of the invention.

The machine computing unit MCU is electronically connected, either analogically or digitally to the non-invasive device D and it is also connected to the actuator A. The connection may be wired or wireless.

The non-invasive device D has the purpose of acquiring endogenously generated electrical potentials within gamma frequency range originating from one or more sources S of gamma waves generated by the brain and/or by the muscles of the body, head, or eyes of the human user and to process the electrical potentials by transforming them into digitized signals to be sent to the machine computing unit MCU. Hereafter, the same simplification as in case of the method will be applied, one source S of gamma waves shall stand for one or more sources S of gamma waves.

The machine computing unit MCU has a first purpose of transforming the digitized signals received from the non-invasive device D in such a way as to carry sufficient information to be processed further for the purpose of converting them into instructions for one or more tasks T to be carried out by the actuator A, and has a second purpose to provide feedback to the human user.

The actuator A has the purpose of carrying out one or more tasks T for the objective for which it was chosen prior to starting the method.

The non-invasive device D comprises two modules: an acquisition and amplification module AAM and a signal recording module REC.

The non-invasive device D may be any device configured to acquire endogenously generated electrical potentials within gamma frequency range, as generated by the brain and/or from the muscles of the body, head, or eyes of the human user. Non-limiting examples of non-invasive devices D are the electroencephalogram EEG, the electromyogram EMG, as well as any single or combined device, regardless of its name, capable to to acquire endogenously generated electrical potentials within gamma frequency range.

Non-invasive devices D typically acquire electrical signals by a plurality of electrodes typically placed on a helmet or on other electrode-carriers, their positioning on the head of the subject being according to the state of art. For the ease of understanding of the invention it shall be assumed that the plurality of electrodes is placed on the helmet.

The method allows using as input the gamma waves generated by the brain and/or from the muscles of the body, head, or eyes of the human user as acquired by the non-invasive device D, a non-limiting example being the combination of electroencephalogram EEG and electromyogram EMG that share the same recording EEG helmet.

The invention may use part of the plurality of electrodes available on the helmet or all the electrodes of the plurality.

The acquisition and amplification module AAM of the non-invasive device D is configured to acquire the endogenously generated electrical potentials within gamma frequency range by one or more source electrodes i $SE_i$ for each source S, each source electrode i $SE_i$ corresponding to carrying out one task T, one or more reference electrodes m $RE_m$, and a selected number of neighboring electrodes j $NE_{ij}$ for each source electrode i $SE_i$.

The selected number of neighboring electrodes j $NE_{ij}$ may encompass the immediate spatial neighbourhood of the respective source electrode i $SE_i$, or a larger neighbourhood on the helmet around the respective source electrode i $SE_i$, including at the limit the plurality of electrodes of the helmet less the respective source electrode i $SE_i$.

Some of the neighboring electrodes j $NE_{ij}$ may be common to more source electrodes i $SE_i$.

The reference electrodes m $RE_m$ may be defined either as dedicated, physical electrodes selected from among the plurality of electrodes, or as a calculated mean potential across all source electrodes i $SE_i$ corresponding to the reference electrode m $RE_m$. More than one reference electrodes m $RE_m$ may be used; for the sake of simplicity one reference electrode $RE_m$ shall stand for one or more reference electrodes m $RE_m$.

FIG. 1 shows one example of placing the electrodes where three sources S are used: two sources from the brain, namely one occipital source $S_{occ}$, located in occipital cortex, one frontal source $S_{fr}$, located in frontal cortex, and one source from the muscles $S_m$. The endogenously generated electrical potentials of the two brain sources $S_{occ}$ and $S_{fr}$ are acquired by the electroencephalogram EEG whereas the endogenously generated electrical potentials of the muscle source $S_m$ are acquired by the electromyogram EMG. The occipital source $S_{occ}$ has two source electrodes $SE_1$ and $SE_2$, the frontal source Sfr has one source electrode $SE_3$, and the muscles source $S_m$ has one source electrode $SE_4$. Source electrodes $SE_1$, $SE_2$ and $SE_3$ share the same reference electrode $RE_1$, whereas the muscles source electrode $SE_4$ has its own reference electrode $RE_2$. Each of the source electrodes $SE_1$, $SE_2$, $SE_3$ and $SE_4$ has two neighboring electrodes j $NE_{ij}$. It shall be understood that the setup of the electrodes depicted in FIG. 1 is for exemplification only and not for limiting the scope of the invention.

The acquisition and amplification module AAM is arranged to amplify the difference between the electrical potentials recorded by each source electrode i $SE_i$ and by its selected number of neighboring electrodes j $NE_{ij}$, on one hand, and a reference, on the other hand, the reference being a function of the electrical potentials recorded by the corresponding at least one reference electrode m $RE_m$. After amplification, the results are the referenced and amplified electrical source and neighboring potentials $AmpEP_{SE_i}$ and $AmpEP_{NE_{ij}}$.

The acquisition and amplification module AAM is arranged to send continuously in time the amplified and referenced electrical source and neighboring potentials $AmpEP_{SE_i}$ and $AmpEP_{NE_{ij}}$ as amplified electrical signals to a signal recording module REC analogically connected to the acquisition and amplification module AAM.

The signal recording module REC is arranged to acquire the amplified electrical signals from the acquisition and amplification module AAM, to low-pass filter the amplified electrical signals for the purpose of antialiasing, and to digitize the amplified and filtered signals with at least 250 samples/s, to buffer the amplified, filtered, and digitized signals, resulting digitized source signals, $DIG_{SE_i}$ and digitized neighboring signals $DIG_{NE_{ij}}$ corresponding to the selected number of neighboring electrodes j $NE_{ij}$.

The signal recording module REC is further arranged to send the digitized source signals, $DIG_{SE_i}$ and digitized neighboring signals $DIG_{NE_j}$ to a signal pre-processing module SPM of a machine computing unit MCU digitally connected to the signal recording module REC. With reference to FIG. 1, the machine computing unit MCU comprises the following modules: the signal pre-processing module SPM, the feature extraction module FEM, the mapping module MAP, the execution module EXC, and the feedback module FED.

The signal pre-processing module SPM is configured to acquire the digitized source signals, $DIG_{SE_i}$ and digitized neighboring signals $DIG_{NE_{ij}}$, and to digitally filter the digitized source signals, $DIG_{SE_i}$ and digitized neighboring signals $DIG_{NE_{ij}}$ by either a band-pass filter, or a notch filter, or both in order to isolate the signals in the gamma frequency range and to eliminate artefacts introduced by the power line e.g., 50 or 60 Hz, such as to output filtered source and respective neighboring signals $FiltDIG_{SE_i}$ and $FiltDIG_{NE_{ij}}$.

The signal pre-processing module SPM is arranged to compute the difference between the filtered digitized source signal $FiltDIG_{SE_i}$ and the weighted average across the set of filtered digitized neighboring signals $FiltDIG_{NE_{ij}}$ such as to output a differential signal $DifSE_i$ for each source electrode i $SE_i$ of the source S, and to send each respective differential signal $DifSE_i$ to a feature extraction module FEM digitally connected to the signal pre-processing module SPM.

The feature extraction module FEM is configured to receive each differential signal $DifSE_i$ corresponding to each source electrode i $SE_i$, and to place at least every 250 milliseconds of each of the differential signal $DifSE_i$ into a corresponding digital buffer, the corresponding digital buffer being configured to be updated at least every 250 milliseconds. At least every 250 milliseconds the feature extraction module FEM is arranged to extract at least one spectral feature of each of the differential signal $DifSE_i$ the at least one spectral feature referring to spectral magnitude, spectral power, spectral phase.

The feature extraction module FEM is configured to calculate at least one numerical descriptor for each of the at least one source electrode i $SE_i$ by using at least one spectral feature referring to spectral magnitude, spectral power, spectral phase or any combination of the spectral features, and to send at least every 250 milliseconds the at least one numerical descriptor to a mapping module MAP of the machine computing unit MCU and simultaneously to a feedback module FED, both digitally connected to the feature extraction module FEM.

Should the calculation of an additional numerical descriptor be envisaged, the feature extraction module FEM may be further configured in a preferred embodiment to extract at least every 250 milliseconds at least one bivariate feature of at least one pair of differential signals $DifSE_{i1}$ and $DifSE_{i2}$, at least one bivariate feature referring to the phase relation between the signals of the at least one pair of differential signals $DifSE_{i1}$ and $DifSE_{i2}$, corresponding to at least two source electrodes i1 $SE_{i1}$ and i2 $SE_{i2}$ and is further configured to calculate at least one numerical descriptor in respect to the at least one bivariate feature.

The feature extraction module FEM may be further configured in another preferred embodiment to extract at least every 250 milliseconds at least one multivariate feature of the differential signal $DifSE_i$, the at least one multivariate feature referring to the entropy, complexity, or fractal dimension across one or more differential signals corresponding to one or more source electrode i $SE_i$ and to compute. at least one numerical descriptor in respect to the multivariate feature or any combination of the multivariate features.

The mapping module MAP is configured to receive at least every 250 milliseconds the at least one numerical descriptor calculated over the features extracted from the differential signal $DifSE_i$ corresponding to each source electrode i $SE_i$, and arranged to associate the at least one numerical descriptor to at least one task T to be carried out by at least one actuator A by defining of at least one instruction.

The mapping module MAP is further arranged to send the at least one instruction via a corresponding action signal to an execution module EXC of the machine computing unit MCU digitally connected to the mapping module MAP.

The mapping module MAP may be further configured in a preferred embodiment to carry out the association either by direct mapping of numerical descriptors onto instructions or by interposing between the numerical descriptors and the instructions at least one classifier, e.g., neural network, support vector machine, decision tree, or any type of classifier, previously trained to perform a specific mapping using machine learning.

The execution module EXC is configured to receive the at least one action signal, to convert the action signal into a digital or analogue instruction signal to be sent to the at least one actuator A electronically connected to the execution module EXC, and to send the instruction signal to the at least one actuator A in order to carry out the at least one task T.

The feedback module FED is analogically or digitally connected to the one actuator A. The feedback module FED comprises a feedback sub-module and a neurofeedback sub-module, both configured to carry out, independently from each other, the feedback operations 8.1. and, respectively, the neurofeedback operations 8.2. of the method.

The feedback sub-module is suitable for carrying out the feedback operation of the method being arranged to receive, for each at least one actuator A, a report signal corresponding to the execution of the at least one task T according to the at least one instruction, to convert the report signal into a feedback signal capable of being transmitted to the human user using any perceptual modality such as visual, auditory, tactile, gustatory, or thermal, and capable of being perceived by the human user, and to send the feedback signal to the human user to be used in next sequences of the method.

The machine computing unit MCU is configured such that the duration of the ensemble operation 5, operation 6, operation 7 and operation 8.1 is less than 750 milliseconds.

The neurofeedback sub-module is suitable for carrying out the neurofeedback operation of the method being arranged to receive at least every 250 milliseconds the at least one numerical descriptor computed by the feature extraction module FEM, to convert the at least one numerical descriptor into a neurofeedback signal capable of being transmitted to the human user using any perceptual modality such as visual, auditory, tactile, gustatory, or thermal, and capable of being perceived by the human user, and to send the neurofeedback signal to the human user to be used in next sequences of the method.

The neurofeedback sub-module is configured in such way that the duration of the ensemble of the three sub-operations—reception of the signal, its conversion into neurofeedback signal and the sending of the feedback signal to the human user—is less than 750 milliseconds.

The machine computing unit MCU is configured such that the feedback operation and the neurofeedback operation are executable independently from each other.

With reference to FIG. 1, the actuator A is electronically connected to the machine computing unit MCU, and is arranged to receive from the execution module EXC of the instruction signal corresponding to the at least one task T, to carry out the at least one task T, and to send to the feedback module FED the report signal about the execution of instruction to carry out the at least one task T according to the at least one instruction.

In another aspect of the invention it is provided a machine computing unit MCU configured to carry out the operations 3 to 6 and operation 8 of the method in order to process endogenously generated electrical potentials within gamma frequency range originating from at least one source S of gamma waves generated by the brain and/or by the muscles of the body, head, or eyes of a human user and to map the potentials into at least one instruction for carrying at least one task T by at least one actuator A.

The machine computing unit MCU according to the invention may be a computing unit such as a computer that is configured to carry out the operations 3 to 6 and operation 8 of the method, the configurations being described in detail throughout the entire specification. The machine computing unit MCU according to the invention may equally be a plurality of computers located remotely from one another, communicating within a computer communication system.

Since the method according to the invention is applied in a distributed computing environment, one computer program is not sufficient for all the three components of the human-machine interface HMI, namely the at least one non-invasive device D, the machine computing unit MCU and the at least one actuator A.

In another aspect of the invention, it is provided a computer program comprising instructions which, when the program is executed by a first computer causes the first computer to encode data by performing operation 1 and 2 of the method and to transmit the encoded data to a second computer.

In another aspect of the invention, it is provided a computer program comprising instructions which, when the program is executed by a second computer causes the second computer to receive encoded data from the first computer and decode the received data by performing operation 3 to 6 of the method, to transmit the encoded data to a third computer for carrying out operation 7 of the method, to receive encoded data from the third computer regarding the execution of operation 7 and decode the received data by performing operation 8 of the method In another aspect of the invention, it is provided a computer program comprising instructions which, when the program is executed by a third computer causes the third computer to receive encoded data from the second computer by performing operation 7 of the method and to transmit the encoded data to the second computer in order to carry out operation 8 of the method.

INDUSTRIAL APPLICABILITY

Hereafter are presented non-limiting examples of fields of application of the invention:

- In the field of healthcare, cosmetics and beauty, the invention may be used for muscle electrostimulation on one or more limbs of the human user.
- In the field of healthcare, the invention may be used to control devices or equipment assisting the patient in moving or carrying out various tasks, such as controlling an exoskeleton, moving a wheelchair, etc. Example of realization No. 1 refers to this field.
- In the field of gaming and entertainment, the invention may be used to control the movement or interaction with real or virtual objects such as: objects used in gaming and entertainment, cursors, pointers, controlling a virtual keyboard, producing sounds and music, etc. Example of realization No. 2 refers to this field.
- In the field of vehicle and equipment control, the invention may be used to carry out various movement tasks for enhanced driving and/or in case of vehicles or equipment to control the movement of the vehicle or equipment itself or parts of the vehicle or equipment, including robots. Example of realization No. 3 refers to this field.
- In the field of aerospace, the invention may be used to control assistive robots or space suits to aid astronauts during extra vehicular activity EVA, commonly known as spacewalk. Example of realization No. 4 refers to this field.

EXAMPLES OF REALIZATION

For a better understanding of the technical teaching of the invention, four non-limiting examples of realization are provided.

Example No.1

In this example, the invention is used for moving a wheelchair by a disabled person, thus the human user is the disabled person. There are two actuators A, namely two motors, one for the left wheel and one for the right wheel sharing together the tasks T corresponding to the actual movements needed: forward T1, backward T2, corner left T3, corner right T4, stop T5. Let us consider two sources S of gamma waves, the sensory-motor cortex on the left hemisphere $S_{SM\_LEFT}$ and the sensory-motor cortex on the right hemisphere $S_{SM\_RIGHT}$. In addition, a third source of gamma waves $S_{JAW}$ corresponds to the muscular contractions of the jaw/maxillary of the human user.

The source electrical potential $EP_{SE_i}$ generated by the three sources S of gamma waves are acquired by three source electrodes $SE_1$, $SE_2$, and $SE_3$, corresponding to $S_{SM\_LEFT}$, $S_{SM\_RIGHT}$, and $S_{JAW}$, respectively. The source electrodes $SE_1$ and $SE_2$ are placed on the scalp over the locations of the left and right sensory-motor cortices of the human user, respectively. The source electrode $SE_3$ is placed on the skin above the right maxillary muscle, directly below the lobe of the right ear.

For both source electrodes $SE_1$ and $SE_2$ additional four neighbouring electrodes $NE_{11}$-$NE_{14}$ and $NE_{21}$-$NE_{24}$, respectively, are placed in a cross configuration with the corresponding source electrode in the centre. For a source electrode, each of its four neighbouring electrodes are placed at a spatial distance of 3 cm from it. Thus, in total there are 10 EEG electrodes recording the source electrical potentials and their neighbours. For $SE_3$ a single neighbouring electrode $NE_3$ is placed at 2 cm below it, on the jaw. The electrodes $SE_3$ and $NE_3$ record electromyogram EMG. In addition to the 10 EEG and 2 EMG electrodes, a single, common reference electrode RE is placed on the top of the scalp, −Cz coordinate in the standard 10-20 EEG montage. In total, the non-invasive device will thus record 10+2+1=13 electrical potentials.

In the first operation of the method, the 12 electrical potentials $SE_1$, $NE_{11}$-$NE_{14}$; $SE_2$, $NE_{21}$-$NE_{24}$; $SE_3$, and $NE_3$ are differentially amplified with respect to the reference potential RE by a differential operational amplifier Damp, continuously in time, such that 12 electrical signals result. The second operation of the method low-pass filters these 12 signals using an electronic filter with cut-off at 300 Hz and then digitizes the 12 signals using an analogue-to-digital converter ADC with sampling rate of 1000 samples/s (1 kHz). In the third operation of the method, the resulting 12 digital signals $DIG_{SE_1}$, $DIG_{NE_{11}}$-$DIG_{NE_{14}}$, $DIG_{SE_2}$, ... are being filtered by two "online" infinite-impulse response IIR filters: a notch at 50 Hz and a band-pass between 30-200 Hz. The resulting filtered digitized source and respective neighbouring signals $FiltDIG_{SE_i}$, $FiltDIG_{NE_{11}}$-$FiltDIG_{NE_{14}}$, $FiltDIG_{SE_2}$, ... are then used to compute in the third sub-operation of the third operation three differential signals, as follows:

i) a first differential signal $DifSE_1$ is computed by subtracting the average across $FiltDIG_{NE_{11}}$-$FiltDIG_{NE_{14}}$ from $FiltDIG_{SE_i}$;

ii) a second differential signal $DifSE_2$ is computed by subtracting the average across $FiltDIG_{NE_{21}}$-$FiltDIG_{NE_{24}}$ from $FiltDIG_{SE_2}$;

iii) a third differential signal $DifSE_3$ is computed by subtracting $FiltDIG_{NE_3}$ from $FiltDIG_{SE_3}$.

The three resulting differential signals $DifSE_1$-$DifSE_3$ are then sent to a feature extraction module FEM. In operation 4 the three resulting differential signals $DifSE_1$-$DifSE_3$ are placed into three corresponding buffers containing 250 samples at every 250 milliseconds, i.e. refreshed 4 times every second. For each of the three buffers the discrete complex Fourier Transform are computed in the first stage of the third sub-operation of operation 4, yielding three frequency-domain representations with 126 values (bins) each, the first bin corresponding to the DC component, while the 126-th bin corresponding to the Nyquist frequency, i.e. 500 Hz. To operate in the gamma frequency range, only frequency bins 9 to 51- that is 43 bins—are retained, which correspond to gamma frequencies from 32 to 200 Hz. Thus, there are three buffers of 43 complex values each, containing the complex Fourier representation. The power as the squared modulus of each complex value is computed, multiplied by 2 corresponding to half-spectrum correction.

At the end of the third sub-operation of operation 4, three vectors are obtained, each containing 43 real-valued numbers corresponding to the power of the differential signals $DifSE_1$-$DifSE_3$ in the gamma frequency range. These vectors are updated every 250 ms, when the three $DifSE_1$-$DifSE_3$ buffers are updated.

Next, three numerical descriptors ND referring to the spectral power are computed in the fourth sub-operation of operation 4 every 250 ms, as follows.

A first numerical descriptor $ND_1$ is calculated by averaging the power bins corresponding to frequency sub-band 32-60 Hz (narrow-band gamma) from the power vector resulting from $DifSE_1$.

Similarly, a second numerical descriptor ND2 is calculated by averaging the power bins corresponding to frequency sub-band 32-60 Hz from the power vector resulting from $DifSE_2$.

A third numerical descriptor ND3, however, is calculated by using a broad-band gamma sub-band by averaging the power bins corresponding to frequency sub-band 32-120 Hz from the power vector resulting from $DifSE_3$.

Thus, values of the numerical descriptors $ND_1$ and ND2 correspond to the average gamma power in the 32-60 Hz range generated in the past 250 ms by sensory-motor sources SSM LEFT and $S_{SM\_RIGHT}$ respectively. The value of the numerical descriptor ND3, on the other hand, represents the broad-band gamma power in the 32-120 Hz range and produced by the right jaw muscle source $S_{JAW}$.

Every 250 ms, the numerical descriptors $ND_1$-ND3 are recalculated and sent to the mapping module MAP in the last sub-operation of operation 4. The mapping module MAP transforms in operation 5 the combination of three numerical descriptors into 5 action codes, each corresponding to one of the 5 tasks T. The mapping is performed according to rules specified in the table below:

| Mapping rule (if test) | Action code from MAP | Corresponding task |
|---|---|---|
| $(ND_1 > 3.0)$ and $(ND_2 > 3.0)$ and $(ND_3 < 1.0)$ | 100 | T1 move forward |
| $(ND_1 > 3.0)$ and $(ND_2 > 3.0)$ and $(ND_3 > 1.0)$ and $(ND_3 < 3.0)$ | 200 | T2 move backward |
| $(ND_1 > 3.0)$ and $(ND_2 < 1.0)$ and $(ND_3 < 1.0)$ | 300 | T3 corner left |
| $(ND_1 < 1.0)$ and $(ND_2 > 3.0)$ and $(ND_3 < 1.0)$ | 400 | T4 corner right |
| $(ND_3 > 3.0)$ | 500 | T5 full stop/safety |

Thus, depending on the particular values of numerical descriptors $ND_1$-ND3 the mapping module MAP will output every 250 ms an action code from 100 to 500, each corresponding to a particular task. To generate these action codes, the disabled person has to:

i) relax the jaw and produce strong gamma in both $S_{SM\_LEFT}$ and $S_{SM\_RIGHT}$ to move forward;

ii) lightly contract the jaw and produce strong gamma in both $S_{SM\_LEFT}$ and $S_{SM\_RIGHT}$ to move backward;

iii) relax the jaw and produce strong gamma only in $S_{SM\_LEFT}$ but not in $S_{SM\_RIGHT}$ to move left;

iv) relax the jaw and produce strong gamma only in $S_{SM\_RIGHT}$ but not in $S_{SM\_LEFT}$ to move right;

v) strongly contract the jaw to make a full stop (this can also be used as a safety feature).

In this example realization the contribution of all three sources is relevant to execute all five tasks and the way the subject entrains gamma power on these sources determines which task will be executed. Importantly, the frequency sub-bands for each of the sources can be adjusted to best match each human user's ability to control the gamma waves.

The action codes generated by the mapping module MAP are then sent in the last sub-operation of operation 5 to the execution module EXC each 250 ms. The execution module EXC will generate in operation 6 the following analogue electrical signals as 5 volts impulses lasting for 500 ms to the left and right motors, as follows:

| Action code from MAP | Output to motor left and motor right | Corresponding task |
|---|---|---|
| 100 | Send 5 V electric signals for 500 ms to both motors | T1 move forward |
| 200 | Send −5 V electric signals for 500 ms to both motors | T2 move backward |
| 300 | Send 5 V electric signal for 500 ms to right motor | T3 corner left |
| 400 | Send 5 V electric signal for 500 ms to left motor | T4 corner right |
| 500 | Cut electric signal to both motors (0 V) | T5 full stop/safety |

Operation 7 of the method refers to the movement of the wheelchair according to the instruction.

The feedback to the human user-the disabled person—is received in operation 8.1 directly via the visual modality as the human user can see the movement of the left and right motors, namely the two actuators A. Because each movement lasts 500 ms, and taking into account the delay in processing the visual stimulus by the brain -~150-200 ms, the feedback about the action reaches the user in less than 750 ms. Given that the numerical descriptors are generated every 250 ms, the full cycle, from the volitional modulation of gamma waves by the human user until the processing of the visual feedback regarding the execution of the action, lasts less than 1000 ms.

To aid the user in controlling his gamma waves, a supplementary neurofeedback is provided in operation 8.2. using sounds. To this end, the feedback module FED receives every 250 ms the three numerical descriptors $ND_1$-ND3. To inform the user about the values of the numerical descriptors, and therefore about the power of gamma waves in the defined bands, a sequence of three tones is generated through speakers that the subject can hear e.g., headphones. Each tone lasts for 30 ms and there is a pause of 50 ms between tones, such that the total sequence ends in less than 240 ms. The frequency of each tone is directly proportional to the value of its corresponding numerical descriptor. As a result, the subject hears tones which inform him about the particular value of each numerical descriptor, learning how strong the gamma waves associated to each of the three sources was in the past 240 ms. The neurofeedback enables the closing of the cycle in 490 ms, that is 250 ms to calculate the numerical descriptors and 240 ms to send the neurofeedback, and helps the subject learn how to control the sources of gamma waves produced by his brain $S_{SM\_LEFT}$ and $S_{SM\_RIGHT}$ and jaw muscle $S_{JAW}$.

One of the great specific advantages of using the method in the field of healthcare is providing the human subject the possibility to move by himself by increasing the number of actuators A and the number of tasks T than can be controlled. In the absence of the invention, the human user of this example of realization, in this case a tetraplegic patient, would not be able to move the wheelchair, thus by applying the invention he gains the possibility to control the movement of the wheelchair. Yet another specific advantage is that the movement of the wheelchair is done in real time. By using the feedback and the neurofeedback, the human subject is trained during the training period until he gains an enhanced control of his gamma waves such that he is able during the operational phase of the method to carry out all the five tasks T.

Example No.2

In the field of gaming and entertainment, the invention may be used to control the movement of real or virtual objects such as: objects used in gaming and entertainment, cursors, pointers, controlling a virtual keyboard, producing sounds and music, etc. The human user is a gamer.

For example, if the game is a flight simulator it may be sufficient to have one actuator A to execute three tasks T: "turn left", "turn right", and "keep straight". The actuator in this case can be a computer game. The execution module EXC can be a program which generates two virtual keycodes, one for "turn left" and one for "turn right", and sends them to the game running on the same computer, instead of using the hand of the human subject to actuate the corresponding keys on the keyboard. The "keep straight" task corresponds to no key code being generated, as the absence of a key press determines the plane to keep its straight trajectory.

The three tasks T of the actuator A are related to the desired movement of the plane from the game to the left, to the right, or going straight, respectively. Depending on the complexity of the game, a single source S may be used, or more sources S. The two cortical sources from example no. 1 are used: the sensory-motor cortex on the left hemisphere $S_{SM\_LEFT}$ and the sensory-motor cortex on the right hemisphere $S_{SM\_RIGHT}$. In this case, the muscular source over the jaw is not necessary. The two source electrodes on the left and right and their neighbouring electrodes are configured identically to example no. 1, i.e. there are 10 electrical potentials recorded by 10 electrodes $SE_1$, $NE_{11}$-$NE_{14}$, $SE_2$, $NE_{21}$-$NE_{24}$, plus one reference electrode RE positioned at the Cz EEG coordinate location. All operations are similar to example no. 1, until the computation of the numerical descriptor ND, which is different.

To calculate the numerical descriptor ND, the feature extraction module EXC first computes the magnitude $M_1$ from the differential signal $DifSE_1$ buffer by averaging the magnitude $M_1$ over frequency bins corresponding to gamma sub-band 32-60 Hz. Then the same procedure is applied on the differential signal $DifSE_2$ buffer to compute magnitude M2, using the same 32-60 Hz gamma sub-band. Thus, $M_1$ and $M_2$ represent the average magnitudes across the 32-60 Hz gamma sub-band originating from sources $S_{SM\_LEFT}$ and $S_{SM\_RIGHT}$, respectively.

For this example, a single numerical descriptor, ND is used, computed from magnitude $M_1$ and magnitude $M_2$, as follows:

$$ND = \begin{cases} -1, \text{ when } (M_1 > M_2) \text{ and } (M_1 > M_T) \\ +1, \text{ when } (M_2 > M_1) \text{ and } (M_2 > M_T) \\ 0, \text{ otherwise} \end{cases}$$

where, $M_T$ is a threshold magnitude determined individually for each human user. One possible procedure to compute $M_T$ is to average the magnitudes $M_1$ and $M_2$ over 10 seconds of data, while the human user remains still and keeps the eyes closed.

The feature extraction module FEM will produce each 250 ms a numerical descriptor ND with a value of −1, +1, or 0, corresponding to "turn left", "turn right", "keep straight", respectively. The mapping module MAP has a very simple job to do in this case, i.e. to convert each number into a virtual key code, as follows: for input −1 generate output code VK_LEFT, that is virtual key code for left arrow key press, for input +1 generate output code VK_RIGHT that is virtual key code for right arrow key press, for input 0 generate output code 0.

The execution module EXC in this case is a specific computer program that receives the codes from the mapping module MAP, grabs focus of the process in which the game is running and injects key press messages into the message queue of that process. In this specific computer program, after gaining process focus, the execution module EXC would do the following: if input is VK_LEFT then generate a WM_KEYDOWN message and inject VK_LEFT key code, if input is VK_RIGHT then generate a WM_KEYDOWN message and inject VK_RIGHT key code, if input is 0 then do nothing as no key is pressed.

The actuator A in this case is the game engine, which renders the flight of the plane and moves it left and right or keeps it flying straight, depending on the key presses it receives from the execution module EXC. The feedback signal in this case is given by the game itself in the form of a rendered image on the monitor, visually informing the human user about the result of executing the particular tasks.

For neurofeedback, the numerical descriptor ND will be associated to a sound tone with three different frequencies, corresponding to ND's value of −1, +1, and 0. This tone will be rendered in the headphones every 250 ms and transmitted to the human user.

The great specific advantage of using the method in the field of gaming and entertainment is the sub-second reaction time which allows for a better gaming experience. The example described above allows up to 4 movements per second, which is faster than what can be obtained by pressing keys using fingers. If the numerical descriptors are generated every 125 ms, then 8 commands per second are possible, which significantly exceeds single key press frequencies achievable by any one finger. Finally, the fast control made possible by the method enables other possible applications in entertainment, like playing a virtual instrument e.g. producing sounds, like a virtual piano, mental games that enhance arousal and therefore gamma oscillations, and so on.

Example No.3

In the field of vehicle and equipment control, the invention may be used to carry out various movement tasks for enhanced driving, control of a vehicle or equipment, or parts of the vehicle or equipment, including robots. In this case, the human user is the operator of the vehicle or equipment. The more complex the vehicle or equipment, the more actuators A are needed and more tasks T are assigned to each actuator A. For example, an earth-moving equipment with various mobile parts, in the absence of the invention, may be controlled using a remote control unit or not. The movement of the various mobile parts of the earth-moving equipment may be partially or totally controlled by a number of actuators A, whereas the tasks T of each mobile part correspond to the movements desired, such as excavate, lift, go forward, go backward, etc. The number of sources S depend on the number of actuators A and on the complexity of the tasks T.

Let's consider an example of a digging excavator that can move at the same time as the operator is picking up dirt and transferring it to a moving truck. Classically, excavators require using all the limbs of the operator, i.e. joysticks for the hands and pedals for the feet as there are multiple joints to be controlled, the rotation of the excavator and so on.

Therefore, with current state of the art it is mostly impossible to have the excavator moving while at the same time digging, loading, rotating, and unloading. The present method allows the extra control of movement, in addition to the classical operation of the excavator. For example, the five tasks from example no. 1 may be added, and the same exact settings for sources and electrodes can be used. The method would be similar to example no. 1 up until the mapping module MAP.

The execution module EXC, the actuators A, and the feedback module FED are different in example no. 3 from example no. 1, as follows.

In case of the excavator, the execution module EXC is a hydraulic controller which can connect each track of the excavator to the engine by a complex gearbox. This controller and the gearbox determine how much power is transferred to each track, and therefore a fast adjustment of the commands in real-time is necessary to steer the excavator on a complex trajectory.

The actuators A in case of the excavator are the two tracks, left and right, which move the excavator.

Due to the position of the cabin, the operator cannot see the tracks underneath and feedback about the movement of the tracks is not always easy to infer from the movement of the excavator. For example, in muddy conditions, a track may slip and therefore the operator does not know if and how much the track is moving by observing the movement of the entire excavator. To provide feedback, the tracks send a signal to the feedback module FED about their rotation speed. Using this signal, the feedback module FED represents the movement of each track as an animation on a monitor in front of the operator, such that the operator can learn how fast each track is moving. For neurofeedback, the operator receives the same tones that are used in example no. 1.

One specific advantage of the invention in this field is that it frees the arms and hands of the operators by providing an extra channel of command of the actuators, which increases the range of the number of actuators and the number of tasks than can be controlled by the operator in the same time and thus enabling the operator to perform a more complex job.

Yet another specific advantage of the invention in this field is that, due to the sub-second reaction time of each sequence of the method, the control of the equipment is quick and the feedback of the control is also quick, thus enabling the operator to perform the job faster.

Yet another specific advantage of the invention in this field is that it allows the user to control actuators for moving equipment in sites where the operator would have to be dressed in a protection suit, which most of the time leads to a severe limitation of the movements of the arms and hands of the operator.

Example No.4

In the field of aerospace, the invention may be used to control assistive robots to aid astronauts during extra vehicular activity EVA. In this case the human user is an astronaut. During EVA, astronauts have to wear heavy and bulky space suits which protect them from the void of space, provide air, thermal insulation, and mechanical protection against micrometeoroids. As a result, the movements possible while the human is in this suit are very limited. In addition, while working on the construction or repair of space stations, the hands of the astronauts have to be used to hold on to the space station to avoid being thrown into space. The lack of gravity is very dangerous and requires a careful and firm hold onto the space station. Furthermore, the peculiarities of spacewalk under zero gravity conditions also render the feet of the astronaut useless for performing any repairing task.

For this example, the application of the invention can be of great use. Consider that a space robot may be controlled directly by the astronaut in order to help with the repairing or building tasks that need to be performed. The astronaut can be close to the actual site of the repairing or building and can coordinate the robot much better that he could while being inside the space station using joysticks, and watching monitors. Let's consider a space robot that can move in 3D and can grab an object with its claw and rotate it clockwise or counter clockwise. The robot can thus perform 10 tasks: move left T1, right T2, up T3, down T4, forward T5, backward T6, close claw T7, open claw T8, rotate claw clockwise T9, rotate claw counter clockwise T10. The actuators A in this case are 6 compressed air valves, which, when open, release pressurized gas thus propelling the robot in the opposite direction one such valve corresponds to each of the 6 movement directions for executing tasks T1-T6. Two additional actuators A are represented by two electric motors that: i) close or open the claw, or ii) rotate the claw clockwise or counter clockwise, depending on the direction of rotation of each motor.

Given that there are 10 tasks to be executed, a large number of sources S is needed. Three sources can be used on the scalp, namely the two sources in example no. 1, over left $S_{SM\_LEFT}$ and right sensory-motor cortices $S_{SM\_RIGHT}$, and one additional source in occipital cortex $S_{OCC}$. These will require 3 source electrodes, each with 4 neighbouring electrodes. In addition, two sources will be used by recording activity from the toes of the left $S_{TOE\_LEFT}$ and the right leg $S_{TOE\_RIGHT}$. Finally, two more sources S will be used from the left jaw $S_{JAW\_LEFT}$ and right jaw $S_{JAW\_RIGHT}$. The four sources corresponding to muscles $S_{TOE\_LEFT}$, $S_{TOE\_RIGHT}$, $S_{JAW\_LEFT}$ and $S_{JAW\_RIGHT}$ will each have one corresponding source electrode and only one neighbouring electrode each, placed similarly as the muscle recording electrodes in example no. 1.

All operations are similar to example no. 1, up until the computation of numerical descriptors. Numerical descriptors will be computed as follows: for each of the 3 cortical sources S, two gamma frequency sub-bands will be used and, for each sub-band, average power will be computed giving 2 numerical descriptors. For example, for source $S_{SM\_LEFT}$ there is a differential signal $DifSE_1$ as input signal to the feature extraction module EXC.

From this signal a first numerical descriptor $ND_{11}$ is computed as the average power in the 32-60 Hz range and a second numerical descriptor $ND_{12}$ as the average power in the 92-120 Hz range. The two numerical descriptors can be used to control movement along the horizontal axis, i.e. left T1 and right T2. The same procedure is applied for signals originating from source SSM_RIGHT to calculate ND2i-move up T3- and ND22-move down T4-, and for signals originating from source $S_{OCC}$ to calculate $ND_{31}$-move forward T5- and ND32-move backwards T6-. Thus, the 3 cortical sources S will control the movement of the robot in 3D.

For each of the four muscular sources one numerical descriptor can be computed in the same way like in example no. 1 corresponding to source $S_{JAW}$ in that example. This will give an additional four numerical descriptors, wherein the ones corresponding to left and right toe muscles will control the closing and opening of the claw, respectively, while the two corresponding to the left and right jaw muscles will rotate the claw clockwise and counter clockwise, respectively.

Feedback can be obtained in this case by direct observation of the robot by the astronaut. In order to transmit neurofeedback to the astronaut there are 10 numerical descriptors to be taken into consideration. However, neurofeedback is critical only for the 6 numerical descriptors originating from cortical sources. For the 4 muscular sources, muscle contractions provide the user direct neurofeedback through proprioceptive sensing. To provide neurofeedback based on the 6 numerical descriptors from cortical sources one may use both tones and visual gauges which are rendered directly on the glass visor of the helmet. These gauges would show up like vertical bars which increase or decrease as a function of the value of the 6 numerical descriptors.

In the case of aerospace, the particulars and the advantages are similar to the ones regarding vehicle and equipment control. It is more likely that in this field actuators A may be controlled uniquely by the method according to the invention because the astronauts have to wear the protective suits which limits severely the movements of their arms and hands. When using the assistive robot, the hands of the astronaut can be freed to be used exclusively for grabbing onto the space station, thus for safety, and for moving around it. By contrast to the previous examples, for the example provided here, a large number of sources S, actuators A and tasks T are required because of the large number of degrees of freedom when working in zero gravity in outer space.

While the description of the method and the system was disclosed in detail in connection to preferred embodiments, those skilled in the art will appreciate that changes may be made to adapt a particular situation without departing from the essential scope to the teaching of the invention.

REFERENCE SIGNS LIST

S source of gamma waves
HMI human-machine interface
D non-invasive device such as EEG electroencephalogram
  EMG electromyogram
AAM acquisition and amplification module
REC signal recording module
i $SE_i$ source electrode i
m $RE_m$ reference electrode m
j $NE_{ij}$ neighboring electrode j
MCU machine computing unit
SPM signal pre-processing module
FEM feature extraction module
MAP mapping module
EXC execution module
FED feedback module
A actuator
T task

The invention claimed is:
1. A method for controlling at least one actuator (A) to carry out at least one task (T) using a human-machine interface (HMI), the method comprising repetitive sequences of operations, the entire duration of each sequence being shorter than 1000 milliseconds, and the method comprising:

acquiring continuously in time, by an acquisition and amplification module (AAM) part of at least one non-invasive device (D), endogenously generated electrical potentials within gamma frequency range originating from at least one source (S) of gamma waves generated jointly by the brain and the muscles of the human user, or independently by the brain or the muscles of the human user, the electrical potentials comprising:

at least one source electrical potential ($EP_{SE_i}$), acquired by at least one source electrode i ($SE_i$) for the at least one source (S) corresponding to carrying out the at least one task (T), a selected number of neighboring electrical potentials ($EP_{NE_{ij}}$) acquired by the same selected number of neighboring electrodes j ($NE_{ij}$) for each of the at least one source electrode i ($SE_i$), and at least one reference electrical potential ($EP_{RE_m}$) acquired by at least one reference electrode ($RE_m$), corresponding to the at least one source electrode i ($SE_i$) and neighboring electrodes j ($NE_{ij}$) of the source electrode, amplifying continuously in time, by the acquisition and amplification module (AAM), the difference between electrical potentials recorded by each source electrode i ($SE_i$) and a selected number of neighboring electrodes j ($NE_{ij}$), and a reference function (RefFunc), the reference function dependent on reference potentials $EP_{RE_m}$ recorded by the corresponding at least one reference electrode m ($RE_m$), and, amplifying the electrical potentials at each source electrode i ($SE_i$) and at its neighboring electrodes j ($NE_{ij}$), by using a differential amplifier (Damp) for each source electrode i ($SE_i$) and each of its neighboring electrodes j ($NE_{ij}$):

$AmpEP_{SE_i} = DAmp(EP_{SE_i} - REF_m)$, $i = \overline{1, NSE}$, $NSE \geq 1$ $AmpEP_{NE_{ij}} = DAmp(EP_{NE_{ij}} - REF_m)$, $j = \overline{1, NNE_i}$, $NNE_i \geq 1$ $REF_m = RefFunc(EP_{RE_m})$, $m = \overline{1, NRE_m}$, $NRE_m \geq 1$ thereby calculating referenced and amplified source electrical potentials ($AmpEP_{SE_i}$) corresponding to each source electrode i ($SE_i$) and referenced and amplified neighboring electrical potentials ($AmpEP_{NE_{ij}}$) which correspond to the selected number of neighboring electrodes j ($NE_{ij}$) of each respective source electrode i ($SE_i$), sending continuously in time the amplified and referenced electrical source and neighboring potentials ($AmpEP_{SE_i}$ and $AmpEP_{NE_{ij}}$) as amplified electrical signals to a signal recording module (REC) part of the at least one non-invasive device (D), acquiring, by the signal recording module (REC), part of the at least one non-invasive device (D), of the amplified electrical signals, low-pass filtering the amplified electrical signals for the purpose of antialiasing, digitizing the amplified and filtered signals with a sampling rate of at least 250 samples per second, and buffering the amplified, filtered, and digitized signals, thereby generating digitized signals, ($DIG_{SE_i}$) corresponding to each source electrode i ($SE_i$) and digitized signals ($DIG_{NE_{ij}}$) corresponding to a selected number of neighboring electrodes j ($NE_{ij}$), and sending to a signal pre-processing module (SPM) of a machine computing unit (MCU) the digitized source signals, ($DIG_{SE_i}$) corresponding to each source electrode i ($SE_i$), and the digitized neighboring signals ($DIG_{NE_{ij}}$) corresponding to its selected number of neighboring electrodes j ($NE_{ij}$), acquiring, by the signal pre-processing module (SPM), of the digitized source and respective neighboring signals ($DIG_{SE_i}$ and $DIG_{NE_{ij}}$);

digitally filtering the digitized source and respective neighboring signals ($DIG_{SE_i}$ and $DIG_{NE_{ij}}$) by either a band-pass filter, or a notch filter, or both in order to isolate the signals in the gamma frequency range and to eliminate artefacts introduced by the power line, thereby generating filtered digitized source and respective filtered digitized neighboring signals ($FiltDIG_{SE_i}$ and $FiltDIG_{NE_{ij}}$);

computing a difference between the filtered digitized source signals ($FiltDIG_{SE_i}$) and a weighted average across filtered digitized neighboring signals ($FiltDIG_{NE_{ij}}$), resulting a differential signal ($DifSE_i$) for each source electrode ($SE_i$) of the at least one source (S);

sending each respective differential signal ($DifSE_i$) to a feature extraction module (FEM);

receiving, by the feature extraction module (FEM), of each the differential signal ($DifSE_i$), placing at least every 250 milliseconds of each of the differential signal ($DifSE_i$) into a corresponding digital buffer, the corresponding digital buffer being updated at least every 250 milliseconds, extracting at least every 250 milliseconds of at least one spectral feature of each differential signal ($DifSE_i$), the at least one spectral feature referring to spectral magnitude, spectral power, spectral phase, for the purpose of quantifying the spectral properties of each respective differential signal ($DifSE_i$) in the gamma frequency range by:

transforming each respective differential signal ($DifSE_i$) from the time-domain into the frequency-domain representation using spectral techniques, and computing the at least one spectral feature referring to spectral magnitude, spectral power, spectral phase of each respective differential signal ($DifSE_i$) from a frequency-domain representation of each differential signal within the gamma frequency range;

calculating at least one numerical descriptor by using the at least one extracted spectral feature and referring to spectral magnitude, spectral power, spectral phase, or any combination of the spectral features, and sending at least every 250 milliseconds the at least one numerical descriptor to a mapping module (MAP) of the machine computing unit (MCU) and, at the same time, sending the at least one numerical descriptor to a feedback module (FED), receiving, by the mapping module (MAP), at least every 250 milliseconds of the at least one numerical descriptor;

associating the at least one numerical descriptor to at least one task (T) to be carried out by at least one actuator (A) by defining of at least one instruction, and sending for the at least one instruction of a corresponding action signal to an execution module (EXC) of the machine computing unit (MCU), receiving, by the execution module (EXC), of the at least one action signal, converting the at least one action signal into a digital or analogue instruction signal to be sent to the at least one actuator (A), and sending the at least one instruction signal to the at least one actuator (A);

receiving, by the at least one actuator (A), of the at least one instruction signal corresponding to the at least one instruction, carrying out the at least one task (T) according to the at least one instruction, and sending a report signal about the execution of the task according to the at least one instruction to the feedback module (FED), receiving, by the feedback module (FED), of the report signal from each at least one actuator (A) in respect to the execution of the at least one task (T) according to the at least one instruction, converting, by the feedback module (FED), the received report signal into a feedback signal capable of being transmitted to the human user using any perceptual modality, and sending the feedback signal to the human user, comprising:

receiving, by the feedback module (FED), at least every 250 milliseconds of the at least one numerical descriptor calculated by the feature extraction module (FEM), converting, by the feedback module (FED), of the at least one numerical descriptor into a neurofeedback signal capable of being transmitted to the human user using any perceptual modality, and sending the neurofeedback signal to the human user.

2. The method of claim 1, wherein computing the difference between the filtered digitized source signal ($FiltDIG_{SE_i}$) and the weighted average across the set of filtered digitized neighboring signals ($FiltDIG_{SE_{ij}}$) satisfies:

$$DifSE_i = FiltDIG_{SE_i} - \sum_{j=1}^{NNE_i} w_j \cdot FiltDIG_{NE_{ij}}, NNE_i \geq 1$$

wherein:
($DifSE_i$) is the resulting differential signal for each source electrode i ($SE_i$) of the at least one source (S);
($FiltDIG_{SE_i}$) is the filtered digitized source signal corresponding to each source electrode i ($SE_i$) of the at least one source (S);
($NNE_i$) is the selected number of neighboring electrodes j ($NE_{ij}$) corresponding to each source electrode i ($SE_i$);
($w_j$) are weighting factors for the neighboring electrodes ($NE_{ij}$);
($FiltDIG_{SE_{ij}}$) are the filtered digitized neighboring signals corresponding to neighboring electrodes j ($NE_{ij}$) of each respective source electrode i ($SE_i$).

3. The system of claim 2, wherein the operations comprise:

extracting at least every 250 milliseconds of at least one multivariate feature of the differential signal ($DifSE_i$), the at least one multivariate feature referring to the entropy, complexity, or fractal dimension across one or more differential signals corresponding to one or more source electrodes i ($SE_i$) by performing operations comprising:

when only one differential signal ($DifSE_i$) is available, embedding in a first stage the one differential signal with a certain time lag to obtain multiple signals, or taking the differential signals ($DifSE_i$) when multiple such signals are available, and computing in a second stage the entropy, complexity, or fractal dimension across the vectors constructed by aggregating the samples at each time point of the multiple signals, and wherein the method further comprises calculating at least one numerical descriptor in respect to the at least one multivariate feature or any combination of the multivariate features.

4. The method of claim 1, comprising extracting at least every 250 milliseconds of at least one bivariate feature of at least one pair of differential signals ($DifSE_{i1}$ and $DifSE_{i2}$) the at least one bivariate feature referring to a phase relation between the signals of the at least one pair of differential signals ($DifSE_{i1}$ and $DifSE_{i2}$) corresponding to at least two source electrodes i1 ($SE_{i1}$) and i2 ($SE_{i2}$) for a purpose of obtaining numerical descriptors which quantify the phase relation between gamma waves generated at different spatial locations across the human user's head or body by performing operations comprising:

transforming the at least one pair of differential signals ($DifSE_{i1}$ and $DifSE_{i2}$) from the time-domain into frequency-domain representation using spectral techniques including the Fourier Transform, Wavelet Transform, or another spectral technique that computes a frequency-domain representation for a time-domain signal, additionally computing the at least one bivariate feature referring to the phase relation between the signals of the at least one pair of differential signals ($DifSE_{i1}$ and $DifSE_{i2}$), and calculating at least one numerical descriptor in respect to the at least one bivariate feature.

5. The method of claim 1, further comprising:

extracting at least every 250 milliseconds of at least one multivariate feature of the differential signal ($DifSE_i$), the at least one multivariate feature referring to the entropy, complexity, or fractal dimension across one or more differential signals corresponding to one or more source electrodes i ($SE_i$) by performing operations comprising:

when only one differential signal ($DifSE_i$) is available, embedding in a first stage the one differential signal with a certain time lag to obtain multiple signals, or taking the differential signals ($DifSE_i$) when multiple such signals are available, and computing in a second stage the entropy, complexity, or fractal dimension across the vectors constructed by aggregating the samples at each time point of the multiple signals, and wherein the method further comprises calculating at least one numerical descriptor in respect to the at least one multivariate feature or any combination of the multivariate features.

6. The method of claim 1 wherein the association is carried out either by direct mapping of numerical descriptors onto instructions or by interposing between the numerical descriptors and the instructions at least one classifier, previously trained to perform a specific mapping using machine learning.

7. A human-machine interface (HMI) for controlling at least one actuator (A) to carry out at least one task (T), the HMI comprising:

at least one non-invasive device (D) comprising:
  an acquisition and amplification module (AAM) arranged to:
    acquire endogenously generated electrical potentials within gamma frequency range originating from at least one source (S) of gamma waves generated by the brain or by the muscles of the body, head, or eyes of a human user by electrodes comprising:
      at least one source electrode i ($SE_i$) for the at least one source (S) corresponding to carrying out the at least one task (T);
      a selected number of neighboring electrodes j ($NE_{ij}$) for each of the at least one source electrode i ($SE_i$); and
      at least one reference electrode ($RE_m$), corresponding to the at least one source electrode i ($SE_i$) and to the neighboring electrodes j ($NE_{ij}$) of the source electrode I;
    amplify a difference between electrical potentials recorded by each source electrode i ($SE_i$) and by a selected number of neighboring electrodes j ($NE_{ij}$) of the source electrode i, and a reference function over electrical potentials recorded by a corresponding at least one reference electrode ($RE_m$), to thereby calculate referenced and amplified electrical source and neighboring potentials ($AmpEP_{SE_i}$ and $AmpEP_{NE_{ij}}$);
    send continuously in time the amplified and referenced electrical source and neighboring potentials ($AmpEP_{SE_i}$ and $AmpEP_{NE_{ij}}$), as amplified electrical signals to a signal recording module (REC) analogically connected to the acquisition and amplification module (AAM);
  the signal recording module (REC) arranged to:
  acquire the amplified electrical signals from the acquisition and amplification module (AAM);
  low-pass filter the amplified electrical signals;
  digitize the amplified and filtered signals with at least 250 samples/s, to buffer the amplified, filtered, and digitized signals, to thereby generate digitized source signals, ($DIG_{SE_i}$) and digitized neighboring signals ($DIG_{NE_{ij}}$) corresponding to the selected number of neighboring electrodesj ($NE_{ij}$);
  send the digitized source signals, ($DIG_{SE_i}$) and digitized neighboring signals ($DIG_{NE_{ij}}$) to a signal pre-processing module (SPM) of a machine computing unit (MCU) digitally connected to the signal recording module (REC);
a machine computing unit (MCU), electronically connected to at least one non-invasive device (D), the machine computing unit (MCU) comprising:
the signal pre-processing module (SPM) configured to:
  acquire the digitized source signals, ($DIG_{SE_i}$) and digitized neighboring signals ($DIG_{NE_{ij}}$);
  digitally filter the digitized source signals, ($DIG_{SE_i}$) and digitized neighboring signals ($DIG_{SE_{ij}}$) by either a band-pass filter, or a notch filter, or both, in order to isolate the signals in the gamma frequency range and to eliminate artefacts introduced by a power line, to thereby output filtered source and respective neighboring signals ($FiltDIG_{SE_i}$ and $FiltDIG_{NE_{ij}}$);
  compute a difference between the filtered digitized source signals ($FiltDIG_{SE_i}$) and a weighted average across their set of filtered digitized neighboring signals ($FiltDIG_{NE_{ij}}$) to thereby output a differential signal ($DifSE_i$) for each source electrode i ($SE_i$) of the at least one source (S); and
  send each respective differential signal ($DifSE_i$) to a feature extraction module (FEM) digitally connected to the signal pre-processing module (SPM);
a feature extraction module (FEM) configured to:
  receive each respective differential signal ($DifSE_i$) corresponding to each source electrode i ($SE_i$);
  place at least every 250 milliseconds of each of the differential signal ($DifSE_i$) into a corresponding digital buffer, the corresponding digital buffer being configured to be updated at least every 250 milliseconds;
  extract at least every 250 milliseconds at least one spectral feature of each differential signal ($DifSE_i$) the at least one spectral feature including spectral magnitude, spectral power, or spectral phase;
  calculate at least one numerical descriptor for each of the at least source electrode i ($SE_i$) by using at least one spectral feature including spectral magnitude, spectral power, or spectral phase or any combination of the spectral features;
  send at least every 250 milliseconds the at least one numerical descriptor to a mapping module (MAP) of the machine computing unit (MCU) and simultaneously to a feedback module (FED), both digitally connected to the feature extraction module (FEM);
a mapping module (MAP) configured to:
  receive at least every 250 milliseconds the at least one numerical descriptor calculated over the features extracted from the differential signal ($DifSE_i$) corresponding to each to each source electrode i ($SE_i$)
  associate the at least one numerical descriptor to at least one task (T) to be carried out by at least one actuator (A) by defining of at least one instruction;
  send for the at least one instruction of a corresponding action signal to an execution module (EXC) of the machine computing unit (MCU) digitally connected to the mapping module (MAP);
an execution module (EXC) configured to:
  receive the at least one action signal;
  convert the action signal into a digital or analogue instruction signal to be sent to the at least one actuator (A) electronically connected to the execution module (EXC); and
  send the instruction signal to the at least one actuator (A) in order to carry out the at least one task (T);
feedback module (FED) electronically connected to the at least one actuator (A) and digitally connected to the feature extraction module (FEM), the feedback module (FED) comprising:
  a feedback sub-module configured to:
    receive for each at least one actuator (A) of a report signal corresponding to an execution of the at least one task (T) according to the at least one instruction;
    convert the report signal into a feedback signal capable of being transmitted to the human user using any perceptual modality capable of being perceived by the human user; and
    send the feedback signal to the human user;
  a neurofeedback sub-module suitable configured to:
    receive at least every 250 milliseconds the at least one numerical descriptor computed by the feature extraction module (FEM);
    convert the at least one numerical descriptor into a neurofeedback signal capable of being transmitted to the human user using any perceptual modality capable of being perceived by the human user;
    send the neurofeedback signal to the human user; and at least one actuator (A) electronically connected to the machine computing unit (MCU), the at least one actuator (A) configured to:
  receive from the execution module (EXC) of the instruction signal corresponding to the at least one task (T);
  execute the at least one task (T); and
  send to the feedback module (FED) the report signal about the execution of the at least one task (T) according to the at least one instruction.

8. The human-machine interface (HMI) of claim 7, wherein the feature extraction module (FEM) is further configured to extract, at least every 250 milliseconds, at least one bivariate feature of at least one pair of differential signals (DifSE$_{i1}$ and DifSE$_{i2}$), the at least one bivariate feature including a phase relation between the signals of the at least one pair of differential signals (DifSE$_{i1}$ and DifSE$_{i2}$), corresponding to at least two source electrodes i1 (SE$_{i1}$) and i2 (SE$_{i2}$) and is further configured to compute at least one numerical descriptor in respect to the at least one bivariate feature.

9. The human-machine interface (HMI) of claim 7, wherein the feature extraction module (FEM) is further configured to extract, at least every 250 milliseconds, at least one multivariate feature of the differential signal (DifSE$_i$), the at least one multivariate feature including the entropy, complexity, or fractal dimension across one or more differential signals corresponding to one or more source electrode i (SE$_i$) and to calculate at least one numerical descriptor in respect to the multivariate feature or any combination of the multivariate features.

10. The human-machine interface (HMI) of claim 7 wherein the mapping module (MAP) is further configured to carry out the association either by direct mapping of numerical descriptors onto instructions or by interposing between the numerical descriptors and the instructions at least one classifier that was previously trained to perform a specific mapping using machine learning.

11. The human-machine interface (HMI) of claim 10, wherein the classifier comprises a neural network, a support vector machine, or a decision tree.

12. The human-machine interface (HMI) of claim 7, wherein the perceptual modality comprises a visual, auditory, tactile, gustatory, or thermal modality.

13. A system comprising:
  one or more processors; and
  one or more machine-readable storage devices storing instructions that are executable by the one or more processors to perform operations for controlling at least one actuator (A) to carry out at least one task (T) using a human-machine interface (HMI), the method comprising repetitive sequences of operations, the entire duration of each sequence being shorter than 1000 milliseconds, and the operations comprising:
  acquiring continuously in time, by an acquisition and amplification module (AAM) part of at least one non-invasive device (D), endogenously generated electrical potentials within gamma frequency range originating from at least one source (S) of gamma waves generated jointly by the brain and the muscles of the human user, or independently by the brain or the muscles of the human user, the electrical potentials comprising:
    at least one source electrical potential (EP$_{SE_i}$) acquired by at least one source electrode i (SE$_i$) for the at least one source (S) corresponding to carrying out the at least one task (T),
    a selected number of neighboring electrical potentials (EP$_{NE_{ij}}$) acquired by the same selected number of neighboring electrodes j (NE$_{ij}$) for each of the at least one source electrode i (SE$_i$), and
    at least one reference electrical potential (EP$_{RE_m}$) acquired by at least one reference electrode (RE$_m$), corresponding to the at least one source electrode i (SE$_i$) and neighboring electrodes j (NE$_{ij}$) of the source electrode,
  amplifying continuously in time, by the acquisition and amplification module (AAM), the difference between electrical potentials recorded by each source electrode i (SE$_i$) and a selected number of neighboring electrodes j (NE$_{ij}$), and a reference function (RefFunc), the reference function dependent on reference potentials EP$_{RE_m}$ recorded by the corresponding at least one reference electrode m (RE$_m$), and,
  amplifying the electrical potentials at each source electrode i (SE$_i$) and at its neighboring electrodes j (NE$_{ij}$), by using a differential amplifier (Damp) for each source electrode i (SE$_i$) and each of its neighboring electrodes j (NE$_{ij}$):

$AmpEP_{SE_i}=DAmp(EP_{SE_i}-REF_m), i=\overline{1,NSE}, NSE \geq 1$ $AmpEP_{NE_{ij}}=DAmp(EP_{NE_{ij}}-REF_m), j=\overline{1,NNE_i}, NNE_i \geq 1$ $REF_m=RefFunc(EP_{RE_m}), m=\overline{1,NRE_m}, NRE_m \geq 1$ thereby calculating referenced and amplified source electrical potentials (AmpEP$_{SE_i}$) corresponding to each source electrode i (SE$_i$) and referenced and amplified neighboring electrical potentials (AmpEP$_{NE_{ij}}$) which correspond to the selected number of neighboring electrodes j (NE$_{ij}$) of each respective source electrode i (SE$_i$),
  sending continuously in time the amplified and referenced electrical source and neighboring potentials (AmpEP$_{SE_i}$ and AmpEP$_{NE_{ij}}$) as amplified electrical signals to a signal recording module (REC) part of the at least one non-invasive device (D),
  acquiring, by the signal recording module (REC), part of the at least one non-invasive device (D), of the amplified electrical signals,
  low-pass filtering the amplified electrical signals for the purpose of antialiasing,
  digitizing the amplified and filtered signals with a sampling rate of at least 250 samples per second, and buffering the amplified, filtered, and digitized signals, thereby generating digitized signals, (DIG$_{SE_i}$) corresponding to each source electrode i (SE$_i$) and digitized signals (DIG$_{NE_{ij}}$) corresponding to a selected number of neighboring electrodes j (NE$_{ij}$), and
  sending to a signal pre-processing module (SPM) of a machine computing unit (MCU) the digitized source signals, (DIG$_{SE_i}$) corresponding to each source electrode i (SE$_i$) and the digitized neighboring signals (DIG$_{NE_{ij}}$) corresponding to its selected number of neighboring electrodes j (NE$_{ij}$),
  acquiring, by the signal pre-processing module (SPM), of the digitized source and respective neighboring signals (DIG$_{SE_i}$ and DIG$_{NE_{ij}}$);
  digitally filtering the digitized source and respective neighboring signals (DIG$_{SE_i}$ and DIG$_{NE_{ij}}$) by either a band-pass filter, or a notch filter, or both in order to isolate the signals in the gamma frequency range and to eliminate artefacts introduced by the power line, thereby generating filtered digitized source and respective filtered digitized neighboring signals (FiltDIG$_{SE_i}$ and FiltDIG$_{NE_{ij}}$);

computing a difference between the filtered digitized source signals and a (FiltDIG$_{SE_i}$) and a weighted average across filtered digitized neighboring signals (FiltDIG$_{SE_{ij}}$), resulting a differential signal (DifSE$_i$) for each source electrode (SE$_i$) of the at least one source (S);

sending each respective differential signal (DifSE$_i$) to a feature extraction module (FEM);

receiving, by the feature extraction module (FEM), of each the differential signal (DifSE$_i$), placing at least every 250 milliseconds of each of the differential signal (DifSE$_i$) into a corresponding digital buffer, the corresponding digital buffer being updated at least every 250 milliseconds, extracting at least every 250 milliseconds of at least one spectral feature of each differential signal (DifSE$_i$), the at least one spectral feature referring to spectral magnitude, spectral power, spectral phase, for the purpose of quantifying the spectral properties of each respective differential signal (DifSE$_i$) in the gamma frequency range by:

transforming each respective differential signal (DifSE$_i$) from the time-domain into the frequency-domain representation using spectral techniques, and computing the at least one spectral feature referring to spectral magnitude, spectral power, spectral phase of each respective differential signal (DifSE$_i$) from a frequency-domain representation of each differential signal within the gamma frequency range;

calculating at least one numerical descriptor by using the at least one extracted spectral feature and referring to spectral magnitude, spectral power, spectral phase, or any combination of the spectral features, and sending at least every 250 milliseconds the at least one numerical descriptor to a mapping module (MAP) of the machine computing unit (MCU) and, at the same time, sending the at least one numerical descriptor to a feedback module (FED), receiving, by the mapping module (MAP), at least every 250 milliseconds of the at least one numerical descriptor;

associating the at least one numerical descriptor to at least one task (T) to be carried out by at least one actuator (A) by defining of at least one instruction, and sending for the at least one instruction of a corresponding action signal to an execution module (EXC) of the machine computing unit (MCU), receiving, by the execution module (EXC), of the at least one action signal, converting the at least one action signal into a digital or analogue instruction signal to be sent to the at least one actuator (A), and sending the at least one instruction signal to the at least one actuator (A);

receiving, by the at least one actuator (A), of the at least one instruction signal corresponding to the at least one instruction, carrying out the at least one task (T) according to the at least one instruction, and sending a report signal about the execution of the task according to the at least one instruction to the feedback module (FED), receiving, by the feedback module (FED), of the report signal from each at least one actuator (A) in respect to the execution of the at least one task (T) according to the at least one instruction, converting, by the feedback module (FED), the received report signal into a feedback signal capable of being transmitted to the human user using any perceptual modality, and sending the feedback signal to the human user, comprising:

receiving, by the feedback module (FED), at least every 250 milliseconds of the at least one numerical descriptor calculated by the feature extraction module (FEM), converting, by the feedback module (FED), of the at least one numerical descriptor into a neurofeedback signal capable of being transmitted to the human user using any perceptual modality, and sending the neurofeedback signal to the human user.

14. The system of claim 13, wherein computing the difference between the filtered digitized source signal (FiltDIG$_{SE_i}$) and the weighted average across the set of filtered digitized neighboring signals (FiltDIG$_{SE_{ij}}$) satisfies:

$$DifSE_i = FiltDIG_{SE_i} - \sum_{j=1}^{NNE_i} w_j \cdot FiltDIG_{NE_{ij}}, NNE_i \geq 1$$

wherein:

(DifSE$_i$) is the resulting differential signal for each source electrode i (SE$_i$) of the at least one source (S);

(FiltDIG$_{SE_i}$) is the filtered digitized source signal corresponding to each source electrode i (SE$_i$) of the at least one source (S);

(NNE$_i$) is the selected number of neighboring electrodes j (NE$_{ij}$) corresponding to each source electrode i (SE$_i$);

(w$_j$) are weighting factors for the neighboring electrodes (NE$_{ij}$);

(FiltDIG$_{NE_{ij}}$) are the filtered digitized neighboring signals corresponding to neighboring electrodes j (NE$_{ij}$) of each respective source electrode i (SE$_i$).

15. The system of claim 13, wherein the operations comprise extracting at least every 250 milliseconds of at least one bivariate feature of at least one pair of differential signals (DifSE$_{i1}$ and DifSE$_{i2}$) the at least one bivariate feature referring to a phase relation between the signals of the at least one pair of differential signals (DifSE$_{i1}$ and DifSE$_{i2}$) corresponding to at least two source electrodes i1 (SE$_{i1}$) and i2 (SE$_{i2}$) for a purpose of obtaining numerical descriptors which quantify the phase relation between gamma waves generated at different spatial locations across the human user's head or body by performing operations comprising:

transforming the at least one pair of differential signals (DifSE$_{i1}$ and DifSE$_{i2}$) from the time-domain into frequency-domain representation using spectral techniques including the Fourier Transform, Wavelet Transform, or another spectral technique that computes a frequency-domain representation for a time-domain signal, additionally computing the at least one bivariate feature referring to the phase relation between the signals of the at least one pair of differential signals (DifSE$_{i1}$ and DifSE$_{i2}$), and calculating at least one numerical descriptor in respect to the at least one bivariate feature.

16. The system of claim 13, wherein the association is carried out either by direct mapping of numerical descriptors onto instructions or by interposing between the numerical descriptors and the instructions at least one classifier, previously trained to perform a specific mapping using machine learning.

* * * * *